(12) United States Patent
Abouzgheib

(10) Patent No.: US 11,690,507 B2
(45) Date of Patent: Jul. 4, 2023

(54) APPARATUS, SYSTEM AND METHOD FOR PERFORMING A BRONCHOSCOPY

(71) Applicant: Thoracent, Inc., Huntington, NY (US)

(72) Inventor: Wissam Abouzgheib, Cherry Hill, NJ (US)

(73) Assignee: Thoracent, Inc., Huntington, NY (US)

( * ) Notice: Subject to any disclaimer, the term of this patent is extended or adjusted under 35 U.S.C. 154(b) by 1391 days.

(21) Appl. No.: 16/001,102

(22) Filed: Jun. 6, 2018

(65) Prior Publication Data
US 2018/0344142 A1 Dec. 6, 2018

Related U.S. Application Data

(60) Provisional application No. 62/515,822, filed on Jun. 6, 2017.

(51) Int. Cl.
*A61B 1/267* (2006.01)
*A61B 1/015* (2006.01)
(Continued)

(52) U.S. Cl.
CPC .......... *A61B 1/2676* (2013.01); *A61B 1/015* (2013.01); *A61M 5/20* (2013.01); *A61M 16/201* (2014.02);
(Continued)

(58) Field of Classification Search
CPC ... A61B 1/2676; A61B 1/00068; A61B 1/015; A61B 1/267; A61B 2017/00973;
(Continued)

(56) References Cited

U.S. PATENT DOCUMENTS 4,648,386 A * 3/1987 Morritt .................... A61B 1/12
604/35
5,582,165 A * 12/1996 Bryan ................. A61M 16/049
128/207.14
(Continued)

FOREIGN PATENT DOCUMENTS

CN 2316968 5/1999
CN 2712272 7/2005
(Continued)

OTHER PUBLICATIONS

International Search Report for Corresponding Application No. PCT/US2018/036195, dated Sep. 17, 2018.
(Continued)

*Primary Examiner* — Katherine H Schwiker
*Assistant Examiner* — Hong-Van N Trinh
(74) *Attorney, Agent, or Firm* — Novel IP

(57) ABSTRACT

A system and method for performing a bronchoscopy. The system may include a bronchoscope, a multi-fluid conduit apparatus, and a switching apparatus. The bronchoscope may include an insertion tube having a distal end, a control section, and a working channel. The multi-fluid conduit apparatus may include a first conduit section operably coupled to a vacuum source, a second conduit section operably coupled to an oxygen source, and a third conduit section operably coupled to the working channel, each of the first and second conduit sections being fluidly coupled to the third conduit section. The switching apparatus may include a valve apparatus operably coupled to each of the first and second conduit sections and an actuator apparatus operably coupled to the valve apparatus. The actuator apparatus may alter the valve apparatus between: (1) a suction supply state; and (2) an oxygen supply state.

8 Claims, 18 Drawing Sheets

(51) Int. Cl.
*A61M 39/10* (2006.01)
*A61M 5/20* (2006.01)
*A61M 16/20* (2006.01)
*A61M 16/00* (2006.01)
*A61B 1/018* (2006.01)
*A61B 1/00* (2006.01)
*A61M 39/22* (2006.01)

(52) U.S. Cl.
CPC ......... *A61M 39/10* (2013.01); *A61B 1/00068* (2013.01); *A61B 1/018* (2013.01); *A61M 16/0096* (2013.01); *A61M 16/20* (2013.01); *A61M 39/223* (2013.01); *A61M 2039/226* (2013.01); *A61M 2202/0208* (2013.01); *A61M 2210/1035* (2013.01); *A61M 2210/1039* (2013.01)

(58) Field of Classification Search
CPC .. A61M 39/223; A61M 16/201; A61M 16/20; A61M 1/0062; A61M 1/772; A61M 2205/078
See application file for complete search history.

(56) References Cited

U.S. PATENT DOCUMENTS

| | | | |
|---|---|---|---|
| 5,735,271 A | 4/1998 | Lorenzen et al. | |
| 5,985,307 A | 11/1999 | Hanson et al. | |
| 7,320,324 B2 | 1/2008 | Willeford | |
| 7,758,541 B2 | 7/2010 | Wallace et al. | |
| 7,892,229 B2 | 2/2011 | Shadduck et al. | |
| 7,985,200 B2 | 7/2011 | Lary et al. | |
| 8,187,269 B2 | 5/2012 | Shadduck et al. | |
| 8,691,216 B2 | 4/2014 | Fraser et al. | |
| 8,858,549 B2 | 10/2014 | Shadduck et al. | |
| 8,974,771 B2 | 3/2015 | Century | |
| 9,198,937 B2 | 12/2015 | Fraser et al. | |
| 9,308,078 B2 | 4/2016 | Weber et al. | |
| 2007/0238929 A1 | 10/2007 | Aizenfeld et al. | |
| 2011/0264004 A1 | 10/2011 | Willeford | |
| 2012/0283630 A1 | 11/2012 | Lee | |
| 2013/0312759 A1 | 11/2013 | Ho | |
| 2014/0142376 A1 | 5/2014 | Ghosh | |
| 2014/0261579 A1* | 9/2014 | Jenkins | A61B 1/12 134/166 C |
| 2017/0043111 A1 | 2/2017 | Hoftman et al. | |
| 2018/0292024 A1* | 10/2018 | Clark | A61C 1/0023 |

FOREIGN PATENT DOCUMENTS

| | | |
|---|---|---|
| CN | 201279131 | 7/2009 |
| CN | 202067715 U | 12/2011 |
| CN | 102019018 | 9/2012 |
| CN | 103645654 A | 3/2014 |
| CN | 203987967 U | 12/2014 |
| CN | 204230118 U | 3/2015 |
| JP | H06277282 A | 10/1994 |
| JP | 2013027638 A | 2/2013 |
| WO | 2017173452 | 10/2017 |
| WO | 2018226783 A1 | 12/2018 |

OTHER PUBLICATIONS

Written Opinion of the International Searching Authority for for PCT/US18/36195, dated Dec. 10, 2018.
International Preliminary Report on Patentability for for PCT/US18/36195, dated Dec. 10, 2018.

* cited by examiner

APPARATUS, SYSTEM AND METHOD FOR PERFORMING A BRONCHOSCOPY

CROSS-REFERENCE TO RELATED APPLICATIONS

The present application claims the benefit of priority to United States Provisional Patent Application Ser. No. 62/515,822, filed Jun. 6, 2017, the entirety of which is incorporated herein by reference.

BACKGROUND OF THE INVENTION

Bronchoscopy involves inserting a scope into a patient's airways and lungs with the patient under intravenous sedation. During a bronchoscopy, patients may suffer from hypoxemia, which is an abnormally low concentration of oxygen in the blood. Hypoxemia cannot be easily reversed during a bronchoscopy because the intravenous sedation directly depresses the respiratory drive of the patient resulting in smaller and less frequent breaths. Furthermore, a common technique during a bronchoscopy is to apply negative pressure suction through the bronchoscope channel to clear secretions in order to have a better visual field and obtain fluid samples. This process literally sucks the air out of the airways which further contributes to the hypoxemia. Traditionally, hypoxemia during a bronchoscopy procedure is treated in one of two ways: (1) by withdrawing the bronchoscope from the patient and providing supplemental oxygen and ventilatory support to the patient; and (2) by applying oxygen at the nose or mouth while the bronchoscope remains in the patient. In either case, the procedure must be stopped or interrupted. With Option (1), the procedure must be restarted by reinserting the bronchoscope into the patient, which is time consuming and can be dangerous. With Option (2), often times it is difficult to get enough oxygen into the lungs to reverse the hypoxemia. Thus, a need exists for a system and method that overcomes these issues and readily enables an operator to reverse hypoxemia without having to remove the bronchoscope from the patient.

SUMMARY OF THE INVENTION

The present invention is directed to an apparatus, system, and/or method for performing a bronchoscopy. The system may include a bronchoscope, a multi-fluid conduit apparatus, and a switching apparatus. The bronchoscope may include an insertion tube having a distal end, a control section, a working channel extending from a first opening in the control section to a second opening in the distal end of the insertion tube, an optical device at the distal end of the insertion tube, and one or more light sources at the distal end of the insertion tube. The multi-fluid conduit apparatus may include a first conduit section operably coupled to a vacuum source, a second conduit section operably coupled to an oxygen source, a third conduit section operably coupled to the working channel, and a flow converger fluidly coupling each of the first and second conduit sections to the third conduit section. The switching apparatus is operably coupled to the multi-fluid conduit apparatus. The switching apparatus may include a valve apparatus operably coupled to each of the first and second conduit sections and an actuator apparatus operably coupled to the valve apparatus. The actuator apparatus may alter the valve apparatus between (1) a suction supply state in which the vacuum source is in fluid communication with the third conduit section and the oxygen source is cut off from fluid communication with the third conduit section; and (2) an oxygen supply state in which the oxygen source is in fluid communication with the third conduit section and the vacuum source is cut off from fluid communication with the third conduit section.

In one embodiment, the invention may be an apparatus for switching between fluid sources during a bronchoscopy, the apparatus comprising: a base; a first tube coupled to the base; a second tube coupled to the base; an actuator apparatus comprising: a first contact portion; and a second contact portion; and wherein the actuator apparatus is alterable between: (1) a first state in which the second contact portion compresses the second tube into occlusion and the first tube is open; and (2) a second state in which the first contact portion compresses the first tube into occlusion and the second tube is open.

In another embodiment, the invention may be an apparatus for switching between fluid sources during a bronchoscopy, the apparatus comprising: a base having a first end and a second end; a first tube coupled to the base and extending from a first end that protrudes a first distance from the first end of the base to a second end that protrudes a second distance from the second end of the base; a second tube coupled to the base and extending from a first end that protrudes a third distance from the first end of the base to a second end that protrudes a fourth distance from the second end of the base; an actuator apparatus alterable between: (1) a first state in which the first tube is open and the second tube is closed; and (2) a second state in which the first tube is closed and the second tube is open; and wherein each of the first, second, third, and fourth distances is five feet or less.

In yet another embodiment, the invention may be an apparatus for switching between fluid sources during a bronchoscopy, the apparatus comprising: a base comprising a first channel having a first opening and a second opening and a second channel having a first opening and a second opening; a first coupling member configured to fluidly couple a first compressible tube to the first channel; a second coupling member configured to fluidly couple a second compressible tube to the second channel; an actuator apparatus comprising: a first contact portion; and a second contact portion; and wherein the actuator apparatus is alterable between: (1) a first state in which the second contact portion is located closer to the base than the first contact portion; and (2) a second state in which the first contact portion is located closer to the base than the second contact portion.

In still another embodiment, the invention may be an apparatus configured for detachable coupling to a bronchoscope to switch between fluid sources during a bronchoscopy, the apparatus comprising: a base having a first channel configured to be fluidly coupled to a vacuum source and a second channel configured to be fluidly coupled to an oxygen source, each of the first and second channels configured to be fluidly coupled to a working channel of a bronchoscope; and a pedal pivotably coupled to the base between: (1) a first state in which the vacuum source is in fluid communication with the working channel of the bronchoscope and the oxygen source is cut off from fluid communication with the working channel of the bronchoscope; and (2) a second state in which the oxygen source is in fluid communication with the working channel of the bronchoscope and the vacuum source is cut off from fluid communication with the working channel of the bronchoscope.

In a further embodiment, the invention may be a system for performing a bronchoscopy, the system comprising: a bronchoscope having a working channel; and a switching apparatus comprising: a base having a first channel configured to be fluidly coupled to a vacuum source and a second channel configured to be fluidly coupled to an oxygen source, each of the first and second channels fluidly coupled to the working channel of the bronchoscope; and a pedal pivotably coupled to the base between: (1) a first state in which the working channel of the bronchoscope is configured to be in fluid communication with the vacuum source and cut off from fluid communication with the oxygen source; and (2) a second state in which the working channel of the bronchoscope is configured to be in fluid communication with the oxygen source and cut off from fluid communication with the vacuum source.

In a still further embodiment, the invention may be a system for performing a bronchoscopy, the system comprising: a bronchoscope having a working channel; and a switching apparatus comprising: a base; a first tube coupled to the base and fluidly coupled to the working channel of the bronchoscope, the first tube configured to be fluidly coupled to a vacuum source; and a second tube coupled to the base and fluidly coupled to the working channel of the bronchoscope, the second tube configured to be fluidly coupled to an oxygen source; and an actuator apparatus comprising: a pedal; a first contact portion; and a second contact portion; and wherein the petal is pivotably coupled to the base between: (1) a first state in which the working channel of the bronchoscope is configured to be in fluid communication with the vacuum source and the second contact portion compresses the second tube into occlusion; and (2) a second state in which the working channel of the bronchoscope is configured to be in fluid communication with the oxygen source and the first contact portion compresses the first tube into occlusion.

In another embodiment, the invention may be a system for performing a bronchoscopy, the system comprising: a bronchoscope comprising: an insertion tube having a distal end; a control section; a working channel extending from a first opening in the control section to a second opening in the distal end of the insertion tube; an optical device at the distal end of the insertion tube; one or more light sources at the distal end of the insertion tube; a multi-fluid conduit apparatus comprising: a first conduit section operably coupled to a vacuum source; a second conduit section operably coupled to an oxygen source; a third conduit section operably coupled to the working channel; a flow converger fluidly coupling each of the first and second conduit sections to the third conduit section; and a switching apparatus operably coupled to the multi-fluid conduit apparatus, the switching apparatus comprising: a valve apparatus operably coupled to each of the first and second conduit sections; and an actuator apparatus operably coupled to the valve apparatus to alter the valve apparatus between: (1) a suction supply state in which the vacuum source is in fluid communication with the third conduit section and the oxygen source is cut off from fluid communication with the third conduit section; and (2) an oxygen supply state in which the oxygen source is in fluid communication with the third conduit section and the vacuum source is cut off from fluid communication with the third conduit section.

In yet another embodiment, the invention may be a method of performing a bronchoscopy, the method comprising: inserting an insertion tube of a bronchoscope into a patient's airways, the insertion tube having a working channel terminating in a second opening in a distal end of the insertion tube; operably coupling a vacuum source to the working channel with a first tube; operably coupling an oxygen source to the working channel with a second tube; and activating a switching apparatus to switch between: (1) compressing the second tube into occlusion to prevent fluid communication between the oxygen source and the working channel while the vacuum source is in fluid communication with the working channel; and (2) compressing the first tube into occlusion to prevent fluid communication between the vacuum source and the working channel while the oxygen source is in fluid communication with the working channel.

In still another embodiment, the invention may be a kit of parts for performing a bronchoscopy, the kit of parts comprising: a package having an interior cavity containing: a switching apparatus for switching between fluid sources during the bronchoscopy; a first tube extending from a first end to a second end; a second tube extending from a first end to a second end; a third tube extending from a first end to a second end; and a flow converger for coupling the first and second tubes to the third tube.

In a further embodiment, the invention may be a method of performing a bronchoscopy, the method comprising: inserting an insertion tube of a bronchoscope into a patient's airways, the insertion tube having a working channel terminating in a second opening in a distal end of the insertion tube; operably coupling a vacuum source to the working channel; operably coupling an oxygen source to the working channel; inserting a working tool into the working channel; and while the working tool remains in-situ within the working channel, activating a switching apparatus to switch between: (1) a suction supply state in which the vacuum source is in fluid communication with the working channel and the oxygen source is cut off from fluid communication with the working channel; and (2) an oxygen supply state in which the oxygen source is in fluid communication with the working channel and the vacuum source is cut off from fluid communication with the working channel.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
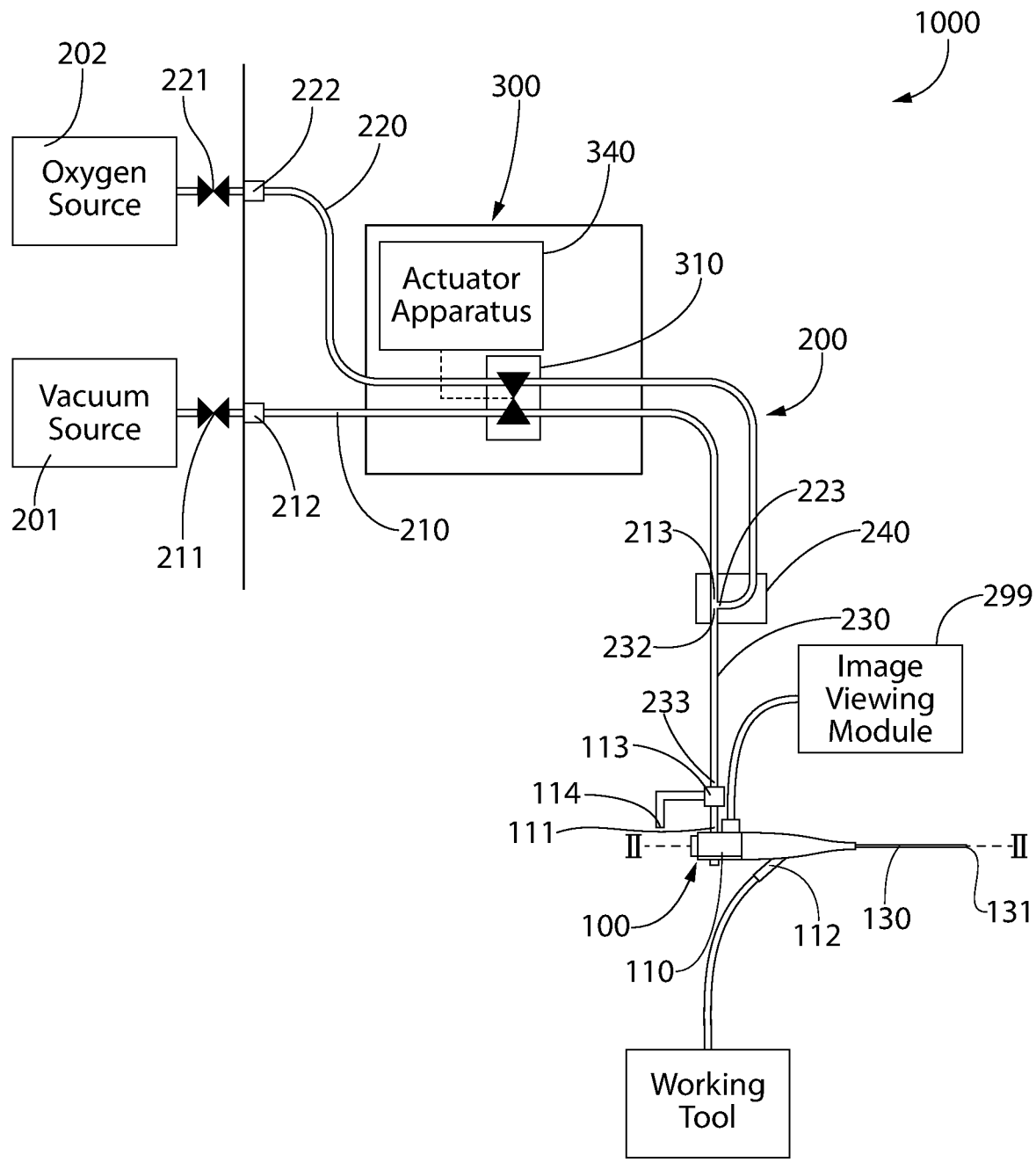
FIG. 1 is schematic illustration of a system for performing a bronchoscope in accordance with a first embodiment of the present invention, the system including a bronchoscope, a multi-fluid conduit apparatus, and a switching apparatus.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Before referring to the figures, the invention will be described in general terms to provide context and a basic understanding of the purpose of the invention. The invention is directed to a system, apparatus, and/or method that enables a bronchoscope operator to switch between various states during a procedure without requiring the operator to remove the bronchoscope from the patient. Specifically, during a bronchoscopy an insertion tube of a bronchoscope is inserted into a patient's airways via the patient's mouth. The insertion procedure is a delicate one, and once the bronchoscope is properly inserted there is a desire to complete the entire procedure without removing the bronchoscope from the patient's airways. Maintaining control of the airway by keeping the bronchoscope within the airway until the procedure is complete is quite desirable and reduces the risk of airway obstruction during the procedure. It helps the operator to maintain airway patency by removing excessive secretions or blood that may block the airways and hinder oxygen and carbon dioxide exchange which could be dangerous in a sedated patient. Thus, maintaining control of the airway by being able to keep the bronchoscope within the airway until the procedure is complete is quite desirable and significantly reduces any risks to the patient.

Once within the patient's airways, the operator can move the distal end of the insertion tube around the throat, larynx, trachea, and lower airways (collectively referred to herein as "the airway" or "the patient's airway") to view these areas to diagnose and/or treat problems. The bronchoscope is typically coupled to a vacuum source to enable the operator to use suction to clear secretions, obtain fluid samples, and for other reasons during the procedure. A patient may suffer from hypoxemia, or a reduction in oxygen saturation, during a bronchoscopy due to a combination of the intravenous sedation and the suction applied during the procedure. The present invention enables an operator to selectively couple the working channel of the bronchoscope to an oxygen source so that an operator can force oxygen back into the patient's lungs easily and without requiring the operator to remove the bronchoscope from the patient's airways. By insufflating oxygen directly into the lungs and bypassing the dead space within the upper airway, hypoxemia can be treated quickly and effectively without slowing down or interrupting the bronchoscopy procedure. Thus, the inventive apparatus, system, and method facilitates the treatment of hypoxemia in situ during the bronchoscopy with minimal action required by the operator.

Figure 2:
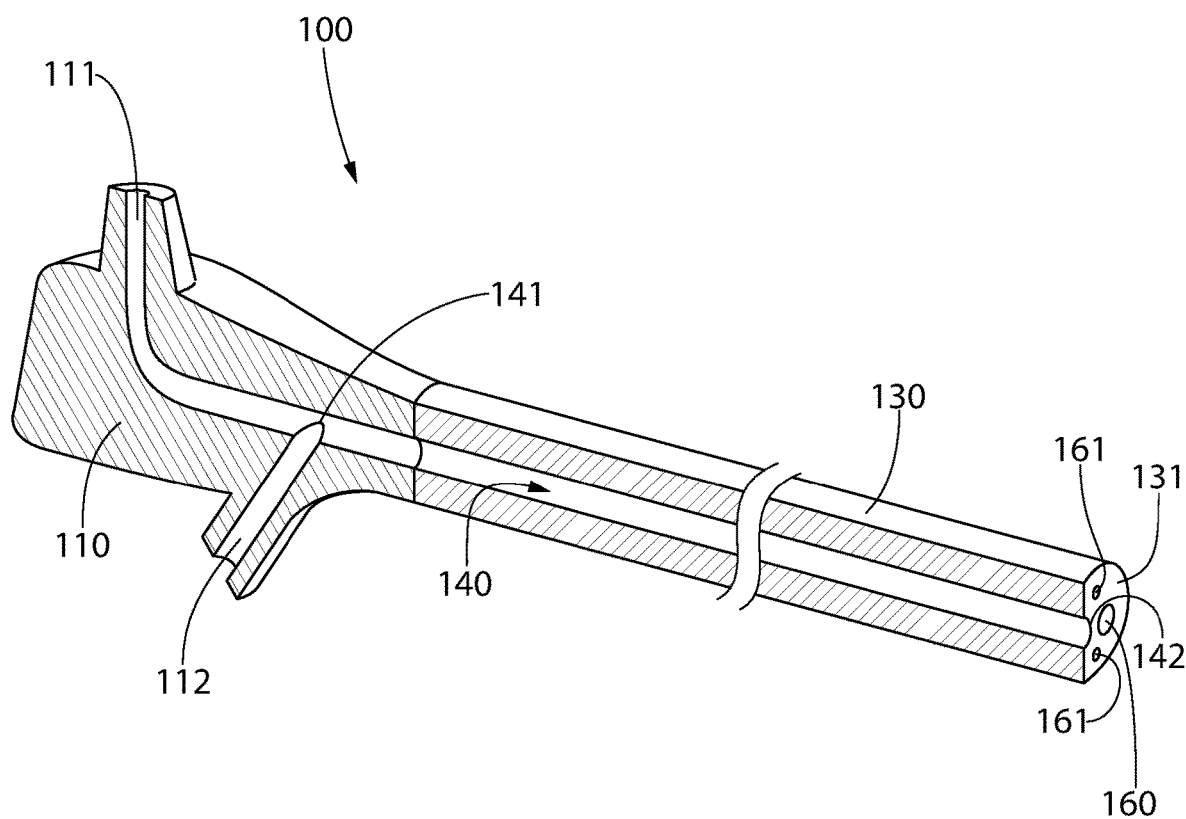
FIG. 2 is a cross-sectional view of the bronchoscope taken along line II-II of FIG. 1.

Referring to FIGS. 1 and 2 concurrently, a system for performing a bronchoscopy 1000 will be described in accordance with an embodiment of the present invention. The system 1000 generally comprises a bronchoscope 100, a multi-fluid conduit apparatus 200, and a switching apparatus 300 for altering the particular fluid that is passed through the multi-fluid conduit apparatus 200, into the working channel of the bronchoscope 100, and into the patient's airways. As will be described in greater detail below with particular reference to FIGS. 6A-12, in some embodiments the invention is directed to the switching apparatus 300 by itself or along with one or more lengths of tube to facilitate the coupling of the switching apparatus 300 to sources of oxygen and vacuum and to the bronchoscope 100. As used herein, a fluid can be a liquid or a gas.

The bronchoscope 100 generally comprises a control section 110, an insertion tube 130 extending from the control section 110 to a distal end 131, and a working channel 140 forming a passageway through at least a portion of the control section 110 and the insertion tube 130. The control section 110 of the bronchoscope 100 comprises a fluid port 111 and an instrument port 112, each of which forms a passageway from the exterior environment to the working channel 140. The working channel 140 extends from a first opening 141 in the control section 110 (where the instrument port 112 intersects the working channel 140) to a second opening 142 in the distal end 131 of the insertion tube 130. Using the system 1000 described herein, vacuum/suction may be applied to the patient's airways or, alternatively, gases such as oxygen and/or liquids such as saline can be insufflated into the patient's airways via the fluid port 111 and the working channel 140. A working tool can be inserted into the patient's airways via the instrument port 112 and the working channel 140 to assist in the bronchoscopy procedure.

The bronchoscope 100 also includes an optical device 160 and one or more light sources 161 located at the distal end 131 of the insertion tube 130 to facilitate obtaining a visual of the patient's airways during a bronchoscopy. The light sources 161 may be halogen, incandescent, or LED type light sources and may be powered via a portable battery or a cable. The optical device 160 may comprise a fiberoptic system that transmits an image from the distal end 131 of the insertion tube 130 to an eyepiece at the opposite end of the bronchoscope 100 or to a monitor that is positioned in a desired location for viewing by the operator. The optical device 160 may be any type of device that can generate an image for viewing by the operator, such as a camera or other image generating device. During use, the optical device 160 may be activated to record video or images that it perceives within the patient's airways. In that regard, the bronchoscope 100 may be operably coupled to an image viewing module 299 so that the operator can view the images being perceived by the optical device 160 for assessment during a bronchoscopy procedure.

The fluid port 111 is operably coupled to the multi-fluid conduit apparatus 200 via a vent coupler 113 to permit fluids to be suctioned/vacuumed out of the patient's airways during a suction operation and/or to permit fluids to be passed into the patient's airways during a fluid supply operation, as will be described in more detail below. Specifically, during a suction supply operation, fluids may pass from the patient's airway, through the working channel 140, through the fluid port 111, and into the multi-fluid conduit apparatus 200. During a fluid supply operation, fluids (i.e., oxygen) may flow from the multi-conduit apparatus 200 into the fluid port 111 of the bronchoscope 100, and from there through the working channel 140 and into the patient's airways. Furthermore, a working tool may be inserted into the working channel 140 via the instrument port 112 and through the second opening 142 into the patient's airways. Non-limiting examples of working tools that may be used with the bronchoscope include a brush, a needle, forceps, or the like.

The vent coupler 113 may be a device that is configured to control whether fluid is supplied to (or suctioned from) the patient's airways or the ambient environment. Specifically, the vent coupler 113 may control whether the multi-fluid conduit apparatus 200, which is coupled to the fluid port 111, is in fluid communication with ambient or with the working channel 140 of the bronchoscope 100. Thus, the vent coupler 113 operates as a type of 3-way valve in that it places the multi-fluid conduit 200 into fluid communication with either ambient or the working channel 140 of the bronchoscope and this can be modified relatively easily by the operator during a bronchoscopy.

In that regard, the vent coupler 113 may comprise a vent outlet 114 and a supply valve (not illustrated). The supply valve may be configured to be alternated between a vent state in which the multi-fluid conduit apparatus 200 is in fluid communication with ambient via the vent outlet 114 and a supply state in which the multi-fluid conduit apparatus 200 is in fluid communication with the working channel 140. Thus, when the multi-fluid conduit apparatus 200 is coupled to a vacuum source as discussed below, fluids may be suctioned from the working channel 140 when the supply valve is in the supply state and from ambient when the supply valve is in the vent state. This enables the vacuum source 201 to always be operational, but not always be suctioning from the patient's airways. The supply valve of the vent coupler 113 may be alternated between the vent state and the supply state by the operator pressing a button, sliding a slide switch, otherwise toggling a switch, or in any other manner. The supply valve may be a mechanical valve or an electric or electromechanical valve in various embodiments. It may be preferable in some embodiments for the operator to be capable of alternating the supply valve of the vent coupler 113 using a single hand.

Figure 3:
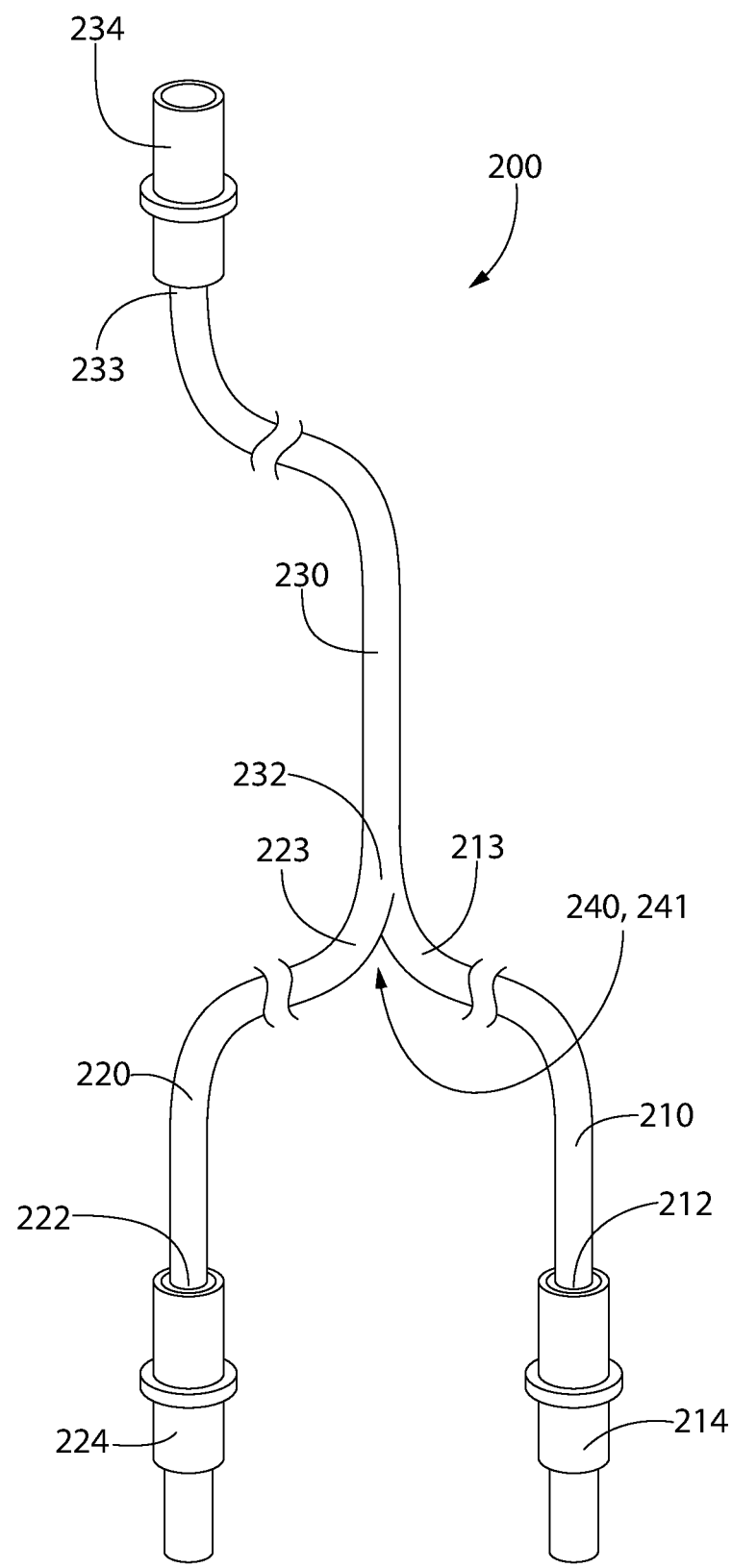
FIG. 3 is an illustration of the multi-fluid conduit apparatus of the system of FIG. 1 in accordance with one embodiment of the present invention.

Referring to FIGS. 1 and 3 concurrently, one exemplary embodiment of the multi-fluid conduit apparatus 200 is illustrated. In certain embodiments, the invention may be directed to the multi-fluid conduit apparatus 200 by itself. Thus, the structural details of the multi-fluid conduit apparatus 200 may form the entirety of the invention without it being required to be coupled to the bronchoscope 100. In other embodiments, the invention may be directed to the multi-fluid conduit apparatus 200 in combination with the switching apparatus 300 without requiring coupling to the bronchoscope 100. In other embodiments the invention may be directed to the switching apparatus 300 by itself or in combination with some additional components disclosed herein.

In some embodiments, the multi-fluid conduit apparatus 200 may be a disposable, one-time use component such that after each bronchoscopy procedure the multi-fluid conduit apparatus 200 is disposed of and replaced with a new multi-fluid conduit apparatus 200 for a bronchoscopy to be performed on a different patient. In that regard, the multi-fluid conduit apparatus 200 or portions thereof as described herein may be formed from medical grade tubing that is relatively inexpensive. The reason that the multi-fluid conduit apparatus 200 may need to be disposable is that patient fluids may pass within the conduits of the multi-fluid conduit apparatus 200 during a bronchoscopy and it may be difficult to satisfactorily sanitize the conduits of the multi-fluid conduit apparatus 200 for its use with another patient. Thus, to avoid possible transmission of disease from patient to patient, it may be desirable or necessary to dispose of the entirety of the multi-fluid conduit apparatus 200 after each use.

The switching apparatus 300 may also be disposable in some embodiments, although it need not be disposable in all embodiments because fluids do not pass through the switching apparatus 300 in all embodiments. In some embodiments, the switching apparatus 300 is a one-time use disposable component such that the switching apparatus 300 is discarded, in its entirety, after each use to prevent patient cross-contamination. The multi-fluid conduit apparatus 200 and the switching apparatus 300 may form a unitary structure in some embodiments. In other embodiments the multi-fluid conduit apparatus 200 may be coupled to and detached from the switching apparatus 300, examples of which will be described herein with reference to FIGS. 6A and 6B. In still other embodiments the switching apparatus 300 may be unitary with portions of the multi-fluid conduit apparatus 200 but not the entirety of the multi-fluid conduit apparatus 200.

The multi-fluid conduit apparatus 200 generally comprises a first conduit section 210 that is operably coupled to a vacuum source 201, a second conduit section 220 that is operably coupled to an oxygen or fluid source 202, and a third conduit section 230 that is operably coupled to the working channel 140 of the bronchoscope 100. The multi-fluid conduit apparatus 200 also includes a flow converger 240 that fluidly couples each of the first and second conduit sections 210, 220 to the third conduit section 230. The switching apparatus 300, which will be described in greater detail below, is operably coupled to the multi-fluid conduit apparatus 200, and specifically to the first and second conduit sections 210, 220 of the multi-fluid conduit apparatus 200.

In this embodiment, each of the first, second, and third conduit sections 210, 220, 230 of the multi-fluid conduit apparatus 200 comprises a length of flexible medical grade tubing. Thus, in some embodiments the first conduit section 210 may be a first tube, the second conduit section 220 may be a second tube, and the third conduit section 230 may be a third tube. Alternatively, each of the first, second, and third conduit sections 210, 220, 230 may comprise multiple tubes that are connected together. The first, second, and third conduit sections 210, 220, 230 may be a unitary construction, or each conduit section may be formed by a separate length of tubing (or multiple lengths of tubing that are connected together with various couplers) with the first, second, and third conduit sections 210, 220, 230 being coupled together to form the multi-fluid conduit apparatus 200. The coupling of the first, second, and third conduit sections (or tubes) 210, 220, 230 together may be achieved using separate coupler components, some of which will be described herein below.

The invention is not to be limited by the first, second, and third conduit sections 210, 220, 230 being formed from medical grade tubing, and in other embodiments the first, second, and third conduit sections 210, 220, 230 may be formed of any material that permits the flow of fluids therethrough as described herein. In various embodiments, the first, second, and third conduit sections 210, 220, 230 may be formed from one or more of, or combinations of, polyurethane, nylon, PVC, polyethylene, Kynar, or the like. Furthermore, the first, second, and third conduit sections 210, 220, 230 are described herein as being flexible, but they may be rigid conduits in other embodiments. However, in certain embodiments described herein there is a preference for at least the first and second conduit sections 210, 220 to be formed from a compressible material so that they can be compressed into occlusion to prevent the flow of fluid therethrough. In some embodiments, compression of the first and second conduit sections 210, 220 is a radial compression such that a portion of the conduit section 210, 220 is forced to collapse radially or in a direction transverse to its longitudinal axis to prevent the flow of fluids through that particular conduit section.

The first conduit section 210 extends from a first end 212 to a second end 213 and has an inner surface defining a passageway from the first end 212 to the second end 213. The second conduit section 220 extends from a first end 222 to a second end 223 and has an inner surface defining a passageway from the first end 222 to the second end 223. The third conduit section 230 extends from a first end 232 to a second end 233 and has an inner surface defining a passageway from the first end 232 to the second end 233. The first end 212 of the first conduit section 210 is coupled to the vacuum source 201 and the second end 213 of the first conduit section 210 is coupled to the first end 232 of the third conduit section 230 (either directly or via the flow converger 240). The first end 222 of the second conduit section 220 is coupled to the oxygen source 202, and the second end 223 of the second conduit section 220 is coupled to the first end 232 of the third conduit section 230 (either directly or via the flow converger 240). The second end 233 of the third conduit section 230 is coupled to the bronchoscope 100, and more specifically to the fluid port 111 and working channel 140 of the bronchoscope 100. Thus, both the vacuum source 201 and the oxygen source 202 are in fluid communication with the working channel 140 of the bronchoscope 100 via the multi-fluid conduit apparatus 200.

The first and second conduit sections 210, 220 are fluidly coupled to the third conduit section 230. Thus, vacuum can be supplied to a patient's airways from the vacuum source 201 collectively via the first conduit section 210, the third conduit section 230, and the working channel 140. Oxygen can be supplied to a patient's airways from the oxygen source 202 collectively via the second conduit section 220, the third conduit section 230, and the working channel 140. In some embodiments, it may be desirable to supply only one of vacuum or oxygen to the patient's airways at a time, and in that regard the switching apparatus 300 may control whether vacuum or oxygen is being supplied at any given time as discussed in more detail below. Thus, in certain embodiments the multi-fluid conduit apparatus 200 in combination with the switching apparatus 300 only permits one of air (oxygen) and suction (vacuum) to be supplied to the patient's airways via the working channel 140 of the bronchoscope 140 at any given time.

In the embodiment exemplified in FIG. 3, the flow converger 240 is a medical grade tube branch 241. Thus, in this embodiment the medical grade tube branch 241 is integrally formed with the medical grade tubing of the first, second, and third conduit sections 210, 220, 230. Specifically, in this embodiment the tubing is manufactured such that the second ends 213, 223 of the first and second conduit sections 210, 220 converge into the first end 232 of the third conduit section 230 without any other components needed to facilitate the convergence. Thus, in this embodiment the multi-fluid conduit apparatus 200 is formed as a single unitary monolithic structure.

A first coupler 214 is operably coupled to the first end 212 of the first conduit section 210. A second coupler 224 is operably coupled to the first end 222 of the second conduit section 220. A third coupler 234 is operably coupled to the second end 233 of the third conduit section 230. In some embodiments, the first, second, and third couplers 214, 224, 234 may be permanently affixed to the first, second, and third conduit sections 210, 220, 230, respectively. This may be achieved by using adhesive, clamps, brackets, welding, mechanical interlocking configurations, or the like. In other embodiments, the first, second, and third couplers 214, 224, 234 may be detachably coupled to the first, second, and third conduit sections 210, 220, 230.

The first, second, and third couplers 214, 224, 234 allow for a simple coupling of the first, second, and third conduit sections 210, 220, 230 to the vacuum source 201, the oxygen source 202, and the bronchoscope 100, respectively, as described herein. Specifically, the first coupler 214 can be readily coupled to the vacuum source 201, the second coupler 224 can be readily coupled to the oxygen source 202, and the third coupler 234 can be readily coupled to the vent coupler 113 or directly to the fluid port 111 of the bronchoscope 100. The couplers 214, 224, 234 may couple the various components together via a friction fit, mechanical interlock, twisted coupling, screw-type coupling, interference fit, snap fit, or the like in various different embodiments and the invention is not to be specifically limited by the type of couplers used in all embodiments.

Moreover, in other embodiments each of the first, second, and third conduit sections 210, 220, 230 may be a separate length of tubing such that they are not integrally connected with one another. In such embodiment, each of the first, second, and third conduit sections 210, 220, 230 may terminate at opposing first and second ends, and a coupler similar to the couplers 214, 224, 234 described above, may be coupled to each of the first and second ends of each of the first, second, and third conduit sections 210, 220, 230. This permits the first, second, and third conduit sections 210, 220, 230 to be readily and easily coupled to and detached from various other components of the system 1000 as described herein.

Figure 4:
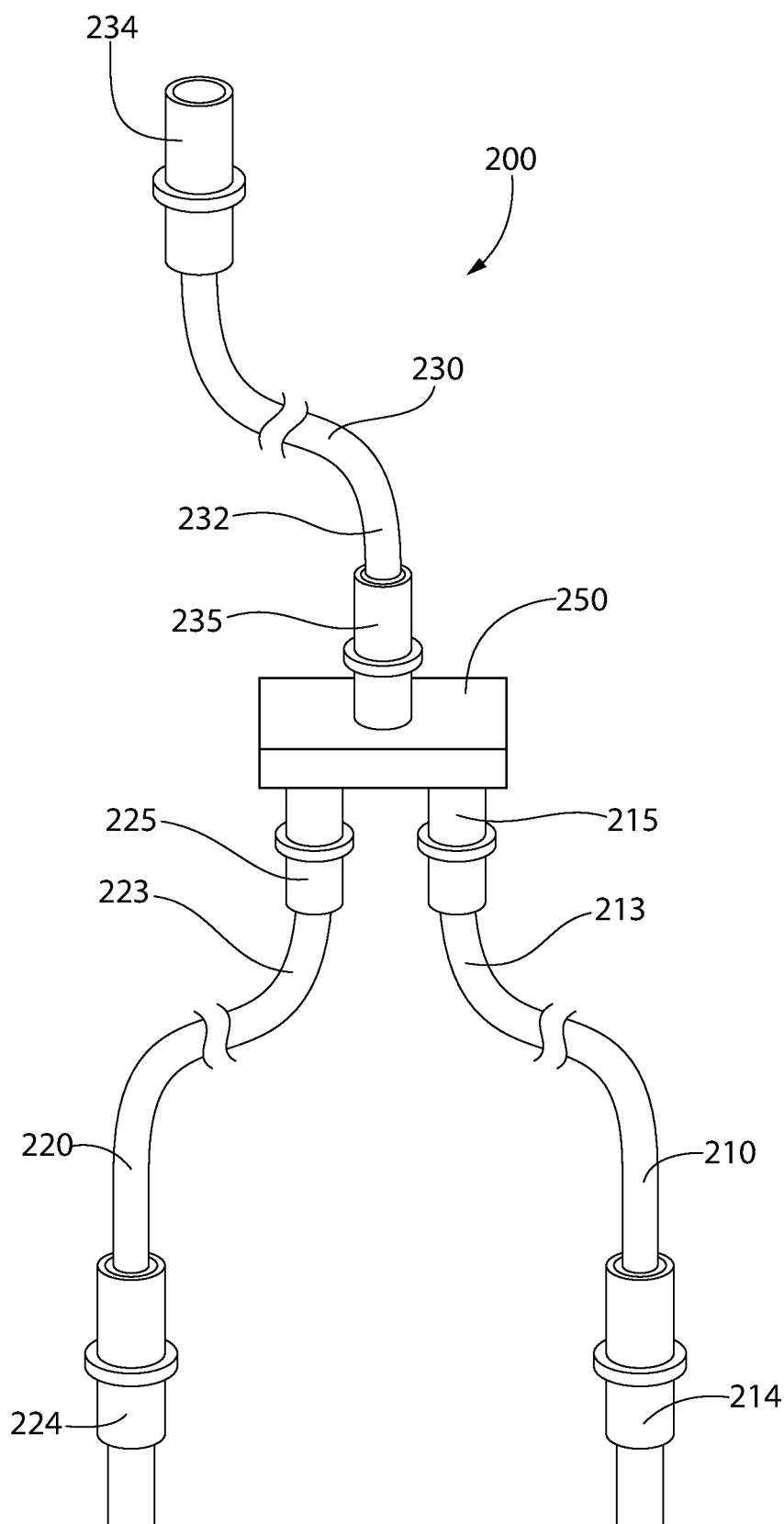
FIG. 4 is an illustration of the multi-fluid conduit apparatus of the system of FIG. 1 in accordance with an alternative embodiment of the present invention.
Figure 5:
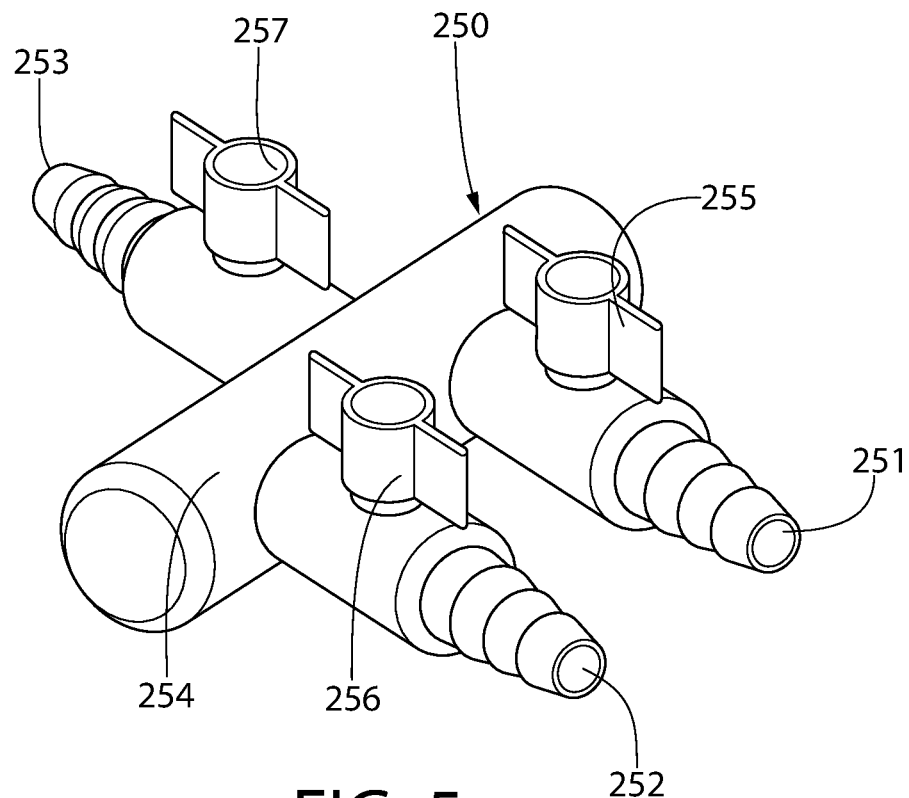
FIG. 5 is a perspective view of a flow converger of the multi-fluid conduit apparatus of FIG. 4.

Referring briefly to FIGS. 1, 4 and 5 concurrently, another exemplary embodiment of the multi-fluid conduit apparatus 200 is illustrated. In this embodiment, the first, second, and third conduit sections 210, 220, 230 are separate components rather than being formed as an integral structure. Thus, each of the first, second, and third conduit sections 210, 220, 230 is formed by a length of tubing that is separate and distinct from the others. Thus, as described above, each of the opposing ends of each of the first, second, and third conduit sections 210, 220, 230 has a coupler. Specifically, the first conduit section 210 has the coupler 214 on one end and a coupler 215 on the other end, the second conduit section 220 has the coupler 224 on one end and a coupler 225 on the other end, and the third conduit section 230 has the coupler 234 on one end and a coupler 235 on the other end. Furthermore, in this embodiment a flow converger 250 fluidly couples each of the first and second conduit sections 210, 220 to the third conduit section 230. More specifically, in this embodiment the flow converger 250 is a manifold device comprising a first port 251, a second port 252, a third port 253, and a manifold section 254. The manifold device may be a plastic housing or casing having various flow passageways that permit each of the first and second ports 251, 252 to be fluidly coupled to the third port 253 so that oxygen or suction can be applied to the working channel 140 of the bronchoscope 100 as described herein.

The second end 213 of the first conduit section 210, and more specifically the coupler thereon 215, is coupled to the first port 251, the second end 223 of the second conduit section 220, and more specifically the coupler 225 thereon, is coupled to the second port 252, and the first end 232 of the third conduit section 230, and more specifically the coupler 235 thereon, is coupled to the third port 253. The manifold section 254 fluidly couples the first and second ports 251, 252 to the third port 253. Thus, if suction/vacuum is being applied to the first conduit section 210, the suction/vacuum will also be applied to the third conduit section 230 (depending on a status of the switching apparatus 300 as discussed in more detail below). Furthermore, if oxygen is being supplied into the second conduit section 220, the oxygen will also be supplied into the third conduit section 230 (depending on the status of the switching apparatus 300 as discussed in more detail below). Because the third conduit section 230 is fluidly coupled to the working channel 140, the oxygen or suction supplied to the third conduit section 230 is also applied to the working channel 140, and hence also to a patient's airways when the bronchoscope 100 is being used for a bronchoscopy procedure.

As shown in FIG. 5, in this embodiment the flow converger 250 may include serrated or barbed connectors at each of the first, second, and third ports 251, 252, 253 to enhance the connection between the first, second, and third conduit sections 210, 220, 230 to the manifold device. Furthermore, the manifold device may include a first valve 255 associated with the first port 251, a second valve 256 associated with the second port 252, and a third valve 257 associated with the third port 253 to open and close the fluid coupling between the first, second, and third ports 251, 252, 253 and the manifold section 254 of the manifold device. The valves 255, 256, 257 are illustrated as being manual or mechanical valves, but any type of valve including electrical valves such as solenoid valves or the like may be used. The type of valve used for the first, second, and third valves 255, 256, 257 is not to be limiting of the present invention in all embodiments (it may be a ball valve, a butterfly valve, a check valve, a diaphragm valve, a plug valve, a piston valve, or any other type of valve now known or later discovered). Furthermore, in other embodiments these valves may be omitted and control of the flow of the fluids may be achieved via the switching apparatus 300 and/or other valves located at other positions along the first, second, and/or third conduits 210, 220, 230.

Figure 5A:
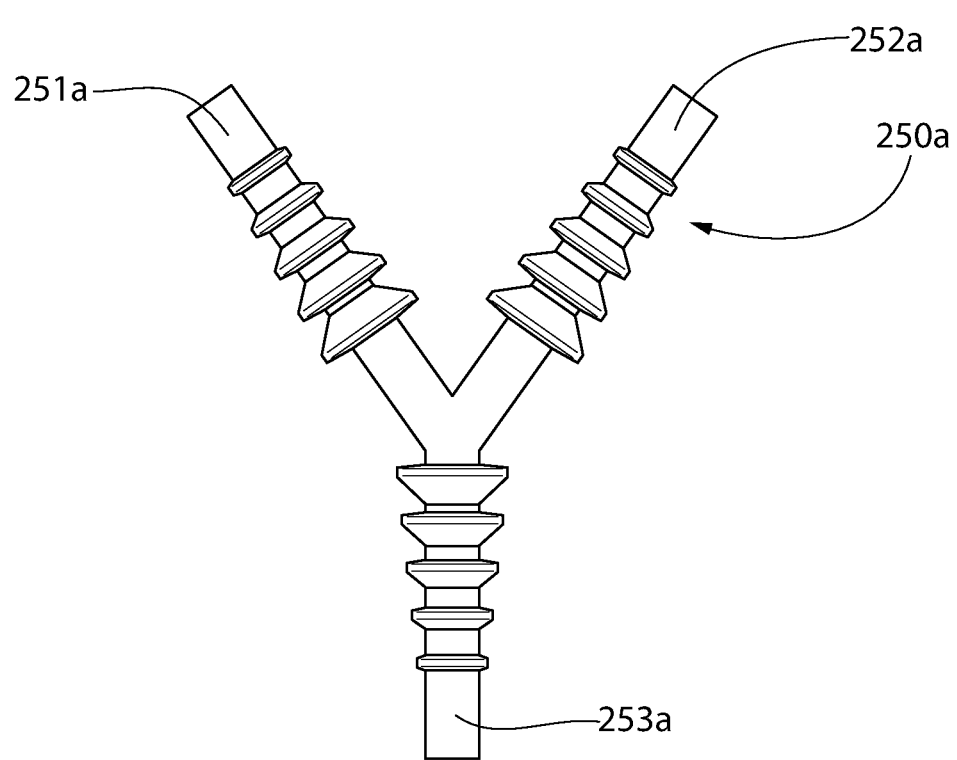
FIG. 5A is a perspective view of a flow converger of the multi-fluid conduit apparatus of FIG. 4 in accordance with another embodiment of the present invention.

FIG. 5A illustrates an alternative embodiment of a flow converger 250a. The flow converger 250a is a Y-type barbed tubing connector that includes a first port 251a, a second port 252a, and a third port 253a. The first, second, and third ports 251a, 252a, 253a are formed at terminal ends of first, second, and third arms of the flow converger 250a. Each of the arms of the flow converger 250a comprises serrations, annular protrusions, barbs, or the like that facilitate retaining a coupling between the flow converger 250a and the one of the first, second, and third conduit sections 210, 220, 230. Specifically, if the first conduit section 210 is coupled to the first arm (the arm terminating at the first port 251a), the first conduit section 210 is not easily separated from the first arm due to the annular protrusions (also referred to in the art as sharkbite protrusions), which prevent the first conduit section 210 from being pulled away from the first leg. The flow converger 250a operates in a similar manner to the flow converger 250 when it is coupled to the various conduits/lengths tubing and thus a more detailed description of the operation of the flow converger 250a and its function is not provided herein, it being understood that the description of the flow converger 250 above is applicable.

Referring back to FIG. 1, in the exemplified embodiment a vacuum supply valve 211 is located along the first conduit section 210 between the vacuum source 201 and the switching apparatus 300 and an oxygen supply valve 221 is located along the second conduit section 220 between the oxygen source 202 and the switching apparatus 300. The vacuum supply valve 211 is alterable between an open state whereby suction is applied into the first conduit section 210 and a closed state whereby no suction is applied into the first conduit section 210. The oxygen supply valve 221 is alterable between an open state whereby oxygen is permitted to flow from the oxygen source 202 into the second conduit section 220 and a closed state whereby oxygen is not permitted to flow from the oxygen source 202 into the second conduit section 220.

Each of the vacuum supply and oxygen supply valves 211, 221 may be manually actuated valves or electrically actuated valves, and the various types of valves noted above are also applicable to these valves. When manually or mechanically actuated, the vacuum supply and oxygen supply valves 211, 221 can be opened and closed manually by an operator or assistant. When electrically actuated, the vacuum supply and oxygen supply valves 211, 221 may be operably coupled to a controller that controls the opening and closing of the vacuum supply and oxygen supply valves 211, 221. The exact type of valve used for the vacuum supply and oxygen supply valves 211, 221 is not to be limiting of the present invention and any valve that is capable of permitting and preventing flow of oxygen and suction as described herein may be used. In other embodiments, the valves 211, 221 may be omitted.

Still referring to FIG. 1, the switching apparatus 300 will be described in general terms. The switching apparatus 300 is operably coupled to the multi-fluid conduit apparatus 200 and comprises a valve apparatus 310 configured to control whether the first and second conduit sections 210, 220 are opened or closed and an actuator apparatus 340 operably coupled to the valve apparatus 210. In some embodiments described herein, the valve apparatus 210 forms a part of the actuator apparatus 340. The actuator apparatus 340 is configured to alter the valve apparatus 310 between: (1) a suction supply state in which the vacuum source 201 is in fluid communication with the third conduit section 230 and the oxygen source 202 is cut off from fluid communication with the third conduit section 230; and (2) an oxygen supply state in which the oxygen source 202 is in fluid communication with the third conduit section 230 and the vacuum source 201 is cut off from fluid communication with the third conduit section 230. Thus, as noted above only one of the vacuum source 201 and the oxygen source 202 is generally fluidly coupled to the third conduit section 230 (and hence also to the working channel 140 of the bronchoscope 100 and the patient's airways) at any given time.

Several different embodiments for the switching apparatus 300 are possible in accordance with the present invention. In that regard, although some specific embodiments are illustrated in the drawings and described herein below, it should be understood that the invention is not to be particularly limited by the exemplified embodiments. Some non-limiting variations and modifications to the exemplified embodiments of the switching apparatus 300 will be mentioned herein below, although it should be appreciated that additional modifications to the switching apparatus 300 are possible and fall within the scope of the present invention disclosed herein. As mentioned above, in some embodiments the switching apparatus 300 may be disposable, although this is not required in all embodiments and it may be a non-disposable device that is operably coupled to the multi-fluid conduit 200 during a bronchoscopy procedure.

Figure 6A:
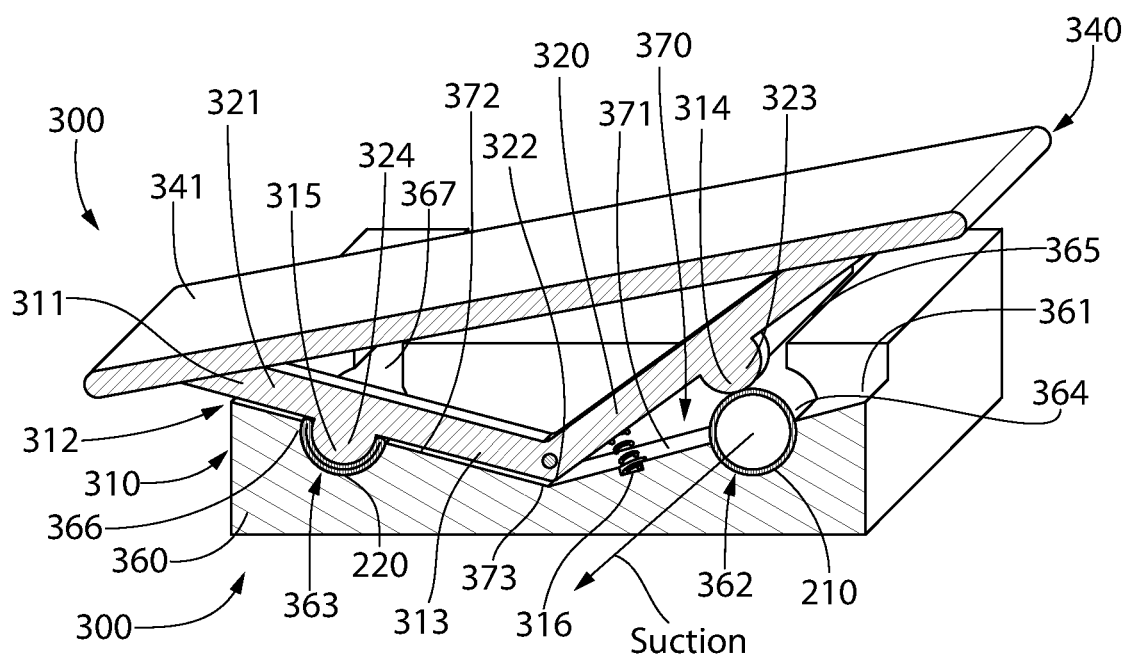
FIG. 6A is a schematic cross-sectional view of the switching apparatus of the system of FIG. 1 in accordance with one embodiment of the present invention, with a valve apparatus of the switching apparatus in a suction supply state.
Figure 6B:
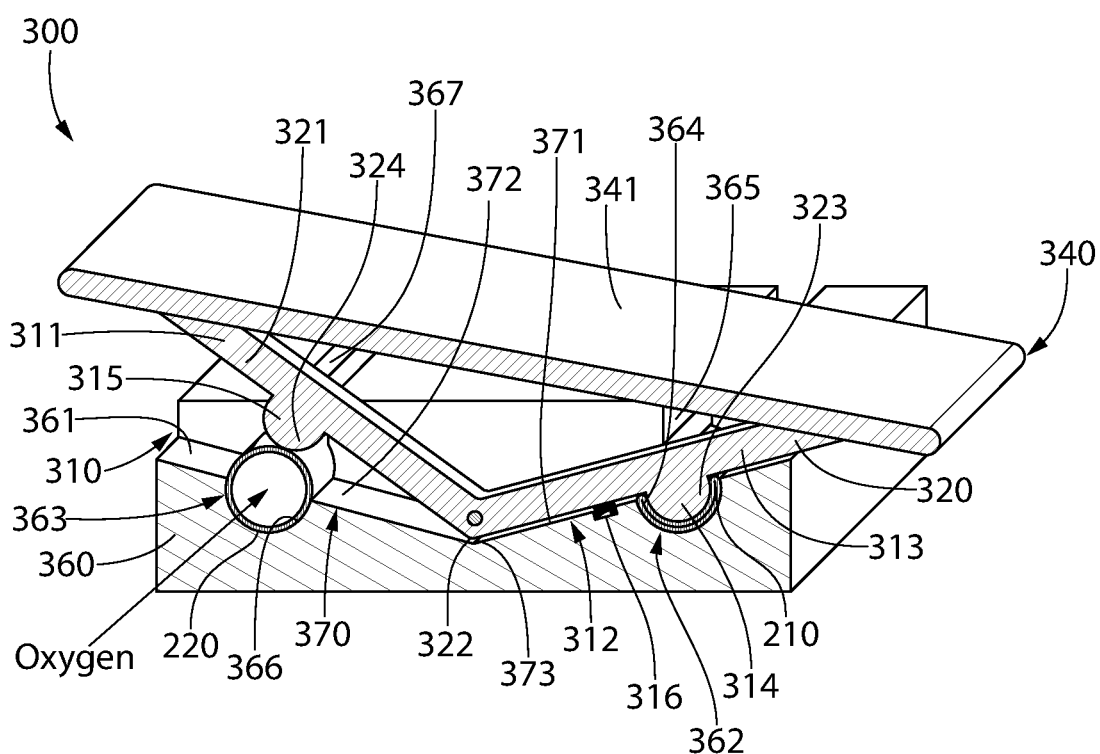
FIG. 6B is a schematic cross-sectional view of the switching apparatus of FIG. 6A with the valve apparatus in an oxygen supply state.

Referring to FIGS. 1 and 6A-6C concurrently, a first embodiment of the switching apparatus 300 will be described. In FIG. 6A the valve apparatus 310 of the switching apparatus 300 is in the suction supply state. In this state, at least a portion of the second conduit section 220 is compressed into occlusion and the first conduit section 210 is open. In FIG. 6B the valve apparatus 310 of the switching apparatus 300 is in the oxygen supply state. In this state, at least a portion of the first conduit section 210 is compressed into occlusion and the second conduit section 220 is open.

As used herein, it should be appreciated that when one of the conduit sections (or tubes) is compressed into occlusion, it is closed such that fluids (i.e., air, oxygen, or the like) generally cannot pass through the occluded section of the conduit. In some embodiments, when a tube is compressed into occlusion is prevents any flow therethrough. Of course, although indicated herein that fluids cannot pass through the occluded section, it may be possible in some embodiments that some of the fluid may still pass through because the tube or conduit section is not fully closed. In some embodiments, when a tube is occluded it prevents fluid communication between the working channel of the bronchoscope and the source that the tube is connecting to the working channel. In some embodiments, this may be prevention of 100% of the fluid, or substantially 100% of the fluid, and in other embodiments this may be prevention of 95%, 90%, 85%, or 80% of the fluid from passing therethrough. In some embodiments, the tube is merely occluded to cut off the supply so that the effective amount of the fluid passing through the non-occluded conduit section is not impacted by the other fluid which is substantially prevented from passing through the occluded conduit section. For example, if one tube supplies suction to the working channel of the bronchoscope and the other tube supplies oxygen to the working channel of the bronchoscope, if the suction tube is closed it should be closed a sufficient amount so that oxygen is still able to pass through the working channel and into the airways without the suction negatively affecting the application of oxygen to the airways. On the other end, if the oxygen tube is closed it should be closed a sufficient amount so that suction is applied to the airways without the oxygen negatively affecting the application of the suction to the airways. This is why an occluded tube should prevent at least 80% of the fluid from passing through that tube.

In certain embodiments, the first and/or second conduit sections 210, 220 may be compressed into occlusion by pinching the conduits a sufficient amount such that fluids such as oxygen and the like cannot pass through the pinched or occluded one of the first and/or second conduit sections 210, 220. In that regard, the tubes of the first, second, and third conduit sections 210, 220 are formed from a flexible/compressible material that enables them to be compressed when a compression force is applied to them. Furthermore, although the exemplified embodiment uses occlusion or pinching of the first and/or second conduit sections 210, 220 to prevent flow of the oxygen or suction therethrough, the invention is not to be so limited in all embodiments. In other embodiments, other valve types can be used such as ball valves or the like that are positioned internally within the passageways of the first and second conduit sections 210, 220 to prevent or enable fluids to pass therethrough.

In this embodiment, the valve apparatus 310 comprises a first valve 311 having a first valve body 312. The valve apparatus 310 further comprises a base 360. The occlusion of the first and second conduit sections 210, 220 occurs as a result of interaction between the first valve body 312 and the base 360 of the valve apparatus 310 with the first and second conduit sections 210, 220 or portions thereof, as discussed more fully herein below. Specifically, portions of the first and second conduit sections 210, 220 may become pinched or sandwiched between the first valve body 312 and the base 360 of the valve apparatus 310 to thereby occlude the pinched one of the first and second conduit sections 210, 220.

In the exemplified embodiment, the actuator apparatus 340 comprises a foot-actuated pedal (or foot platform) 341 such that a user can alter the valve apparatus 310 between the suction supply and oxygen supply states using his or her foot by pivoting the pedal 341 relative to the base 360 as discussed further herein below. More specifically, as noted above the valve apparatus 310 may form a part of the actuator apparatus 340. In that regard, the valve apparatus 310 may form a part of the pedal 341 or it may be coupled to the pedal 341. Thus, as a user actuates the actuator apparatus 340 by pivoting the pedal 341, the user simultaneously adjusts the valve body 312 between a first state (i.e., the suction supply state) in which the valve body 312 compresses the second conduit section 220 and leaves the first conduit section 210 open, and a second state (i.e., the oxygen supply state) in which the valve body 312 compresses the first conduit section 210 and leaves the second conduit section 220 open.

In the exemplified embodiment, the base 360 comprises an upper surface 361, a first conduit receiving section 362 formed into the upper surface 361 and a second conduit receiving section 363 formed into the upper surface 361. More specifically, the first conduit receiving section 362 comprises a first channel 364 formed into the upper surface 361 of the base 360 and a first entry slot 365 extending from the first channel 364. Similarly, the second conduit receiving section 363 comprises a second channel 366 formed into the upper surface 361 of the base 360 and a second entry slot 367 extending from the second channel 366. The first entry slot 365 has a width that is less than the width of the first channel 364 and the second entry slot 367 has a width that is less than the width of the second channel 366.

The first conduit section 210 of the multi-fluid conduit apparatus 200 nests within the first channel 364 of the first conduit receiving section 362. Because the first entry slot 365 has a width that is less than the width of the first channel 364, the first conduit section 210 may be forced through the first entry slot 365 (which may be possible due to the flexible nature of the first conduit section 210 in some embodiments). In other embodiments, the first conduit section 210 may be translated or slid into the first channel 364 along the longitudinal axis of the first channel 364 without having to pass through the first entry slot 365. Once positioned within the first channel 364, the first conduit section 210 cannot be readily removed therefrom, but rather must be forced back through the first entry slot 365 which requires some force being applied by an operator or translated along the longitudinal axis of the first channel 364 until it is completely removed from the first channel 364.

The second conduit section 220 of the multi-fluid conduit apparatus 200 nests within the second channel 366 of the second conduit receiving section 363. Because the second entry slot 367 has a width that is less than the width of the second channel 366, the second conduit section 220 may be forced through the second entry slot 367 (which may be possible due to the flexible nature of the second conduit section 220 in some embodiments) In other embodiments, the second conduit section 220 may be translated or slid into the second channel 366 along the longitudinal axis of the second channel 366 without having to pass through the second entry slot 367. Once positioned within the second channel 366, the second conduit section 220 cannot be readily removed therefrom but rather must be forced back through the second entry slot 367 which requires some force being applied by an operator or translated along the longitudinal axis of the second channel 366 until it is completely removed from the second channel 366.

Thus, in the exemplified embodiment the first and second entry slot sections 365, 367 function as first and second conduit retaining elements, respectively, in that they retain the first and second conduit sections 210, 220 in the first and second conduit receiving sections 362, 363. Of course, the invention is not to be so limited in all embodiments and in other embodiments the first and second conduit retaining elements may be selected from a group consisting of a clamp, a latch, a bracket, a surface of the base 360, a block, or any other device or mechanism that facilitates keeping the first and second conduit sections 210, 220 in position. In some embodiments, it is possible for the first and second channels 364, 366 to be omitted and for the first and second conduit sections 210, 220 to rest atop the top surface 361 of the base 360 and to be secured to the base 360 using clamps, latches, brackets, or the like. Moreover, in still other embodiments the first and second conduit sections 210, 220, or portions thereof, may be formed integrally with the base 360 or may otherwise be permanently fixed to the base 360 so that they cannot be detached therefrom.

In certain embodiments, the multi-fluid conduit apparatus 200 can be replaced simply by removing the first and second conduit sections 210, 220 from the first and second conduit receiving sections 362, 363 and nesting the first and second conduit sections 210, 220 of a new multi-fluid conduit 200 within the first and second conduit receiving sections 362, 363. Thus, the switching apparatus 300 may not be disposable, but the multi-fluid conduit 200 may be disposable. Thus, the multi-fluid conduit 200 may be readily detached from the switching apparatus 300 and a new multi-fluid conduit 200 may be readily attached to the switching apparatus 300. This enables the relatively inexpensive tubing that contacts body fluid to be replaced while the more expensive switching apparatus 300 that includes moving parts is not replaced. In other embodiments, the multi-fluid conduit 200 and the switching apparatus 300 may be fixedly coupled together such that they are both disposed together after each use and replaced with a new multi-fluid conduit 200 and switching apparatus 300. This version may be desirable for its ease of use because it won't require an end-user to detach and reattach tubes to the switching apparatus 300 for subsequent operations.

In the exemplified embodiment, the first valve body 312 comprises a rocker 313 extending from the pedal 341. In the exemplified embodiment, the first valve body 312, and hence also the rocker 313, is integrally formed with the pedal 341 as a monolithic component. In the exemplified embodiment the upper surface 361 of the base 360 has a recessed portion 370 comprising a first sloped portion 371 and a second sloped portion 372 that meet at an apex 373. The rocker 313 comprises a first arm 320 extending from a first side of the pedal 341 and a second arm 321 extending from a second side of the pedal 341. The first and second arms 320, 321 are connected at an apex 322 that nests within the apex 373 of the upper surface 361 of the base 360.

Furthermore, in the exemplified embodiment the rocker 313 comprises a first contact section (or first contact portion) 314 and a second contact section (or second contact portion) 315. Specifically, in the exemplified embodiment the first contact section 314 is formed by a first protuberance 323 extending from the first arm 320 and the second contact section 315 is formed by a second protuberance 324 extending from the second arm 321. In the exemplified embodiment, each of the first and second protuberances 323, 324 has a convex outer surface, although other structural implementations are possible in other embodiments. During use, the first contact section 314 interacts with the first conduit section 210 to occlude the first conduit section 210 during the oxygen supply state and the second contact section 315 interacts with the second conduit section 220 to occlude the second conduit section 220 during the suction supply state. Specifically, the rocker 313 is configured to rock back and forth within the recessed portion 370 of the base 360 to alternate between the suction supply state (FIG. 6A) and the oxygen supply state (FIG. 6B). In some embodiments, the first and second contact sections 314, 315 interact with a support surface of the base 360 to achieve the desired occlusion. Thus, in the suction supply state the second conduit section/tube 220 is compressed between the second contact portion 315 and the support surface of the base 360 and in the oxygen supply state the first conduit section/tube 210 is compressed between the first contact portion 314 and the support surface of the base 360.

However, it should be appreciated that the arrangement of the various components as depicted in the exemplified embodiment are not limiting of the present invention in all embodiments. It is possible that in alternative embodiments, the first and second contact portions 314, 315 may be flanges, lips, or the like that extend from edges of the pedal 341 so that the first and second contact portions 314, 315 can occlude the first and second conduit sections 210, 220 as described herein depending on the actuated state of the pedal 341. Regardless, in some embodiments the actuator apparatus 340 comprises the first and second contact portions 314, 315 and in some embodiments the pedal 341 comprises the first and second contact portions 314, 315.

Returning to the exemplified embodiment, the first valve body 312 can be altered by the actuator apparatus 340 between: (1) a first position in which the first valve body 312, and more specifically the first contact portion 314, compresses the second conduit section 220 into occlusion and the first conduit section 210 is open; and (2) a second position in which the first valve body 312, and more specifically the second contact portion 315, compresses the first conduit section 210 into occlusion and the second conduit section 220 is open. Specifically, the rocker 313 is pivotably coupled to the base 360 between a first position, illustrated in FIG. 6A, in which the second contact portion 315 compresses the second conduit section 220 into occlusion and a second position, illustrated in FIG. 6B, in which the first contact portion 314 compresses the first conduit section 210 into occlusion. In FIG. 6A, suction is permitted to be supplied into the first conduit section 210 and from there into the third conduit section 230 while oxygen is prevented from flowing from the second conduit section 220 to the third conduit section 230 due to the occlusion of the second conduit section 220. In FIG. 6B, suction is prevented from being supplied from the first conduit section 210 to the third conduit section 230 due to the occlusion of the first conduit section 210 while oxygen is permitted to flow from the second conduit section 220 to the third conduit section 230 due to the second conduit section 220 not being occluded or otherwise closed.

In the exemplified embodiment, the first conduit section 210 extends along a first axis A-A and the second conduit section 220 extends along a second axis B-B. The first and second axes A-A, B-B are parallel to one another in the exemplified embodiment but may be oblique in others. Furthermore, in the exemplified embodiment the pedal 341 pivots between the first and second states (i.e., the suction supply and oxygen supply states, respectively) about a pivot axis C-C that is parallel to the first and second axes A-A, B-B. However, the invention should not be so limited in all embodiments and the switching apparatus 300 could be reconfigured in such a way so that the pedal 341 pivots about a pivot axis that is perpendicular to the first and second axes A-A, B-B to transition between the first and second states. Thus, various alterations, modifications, or the like are possible and would still fall within the scope of the invention as defined herein.

Figure 6C:
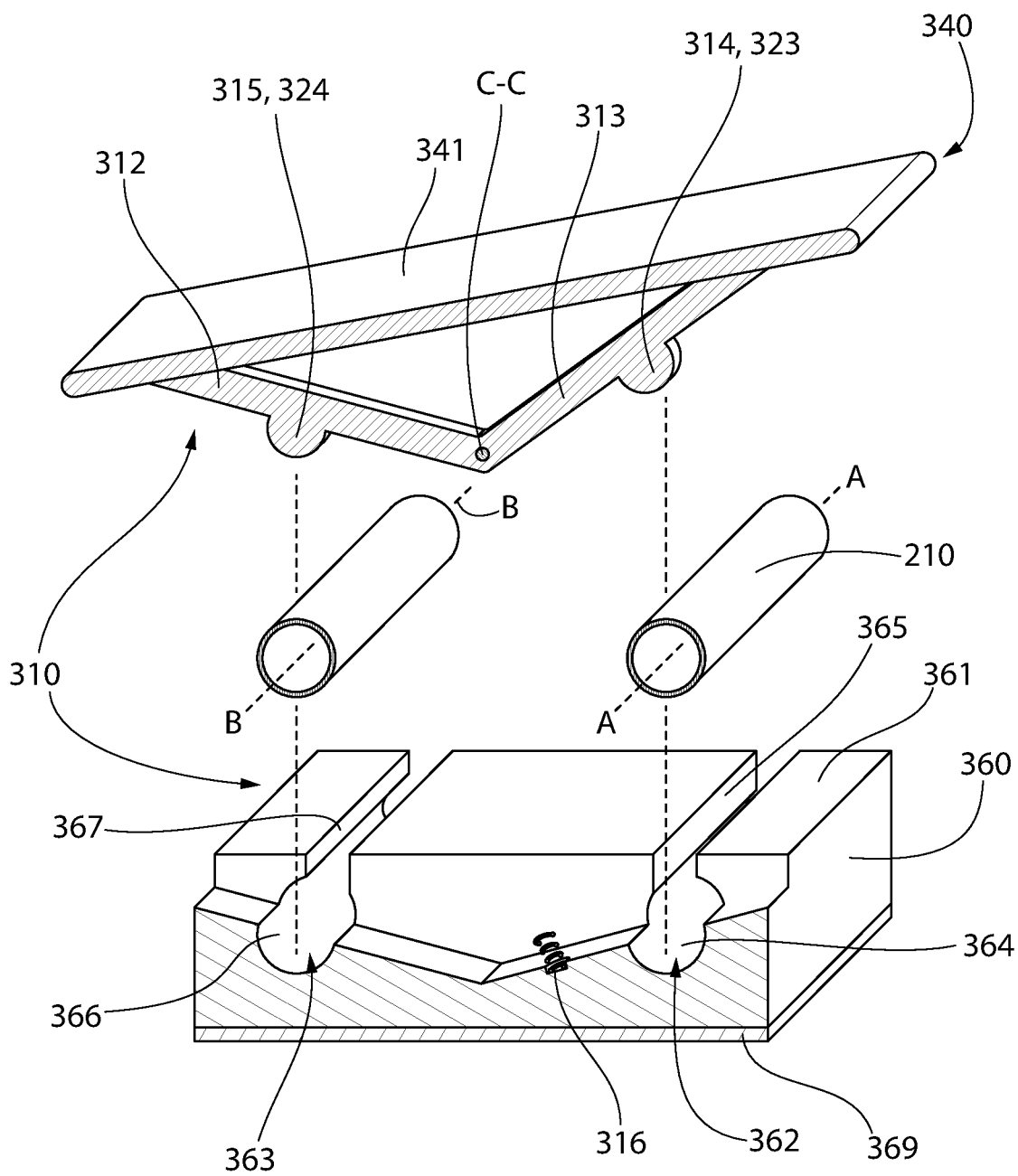
FIG. 6C is an exploded view of the switching apparatus of FIG. 6A.

As shown only in FIG. 6C, the base 360 may include a layer of material 369 on its bottom surface to facilitate holding the base 360 in place during use. The layer of material 369 may be a rubber or similar material that would create friction with the floor to prevent the base 360 from moving during use. Alternatively, the layer of material 369 could be an adhesive layer with a release layer that is removed by a user/operator prior to performing a bronchoscopy to hold the base 360 in place in a desired location.

Viewing FIGS. 1, 6A, and 6B concurrently readily shows how the suction or oxygen will or will not flow into the working channel 140 of the bronchoscope 100 and from there into the patient's airways depending on which of the first and second conduit sections 210, 220 is occluded or otherwise closed as described herein. Specifically, as seen in FIG. 1, if the first conduit section 210 is open, fluid communication is open from the vacuum source 201 to the bronchoscope 100 and thus suction can be pulled from a patient's airways. To the contrary, if the first conduit section 210 is occluded or closed, the vacuum source 201 is not in fluid communication with the bronchoscope 100 and vacuum will not flow from the first conduit section 210 to the third conduit section 230, and thus no suction will be applied to the patient's airways. If the second conduit section 220 is open, fluid communication is open from the oxygen source 202 to the bronchoscope 100 and thus oxygen can be supplied into the patient's airways. If the second conduit section 220 is occluded or closed, the oxygen source 202 is not in fluid communication with the bronchoscope 100 and oxygen will not flow from the second conduit section 220 to the third conduit section 230, and thus no oxygen will be instilled into the patient's airways.

In the exemplified embodiment the valve apparatus 310 also includes a resilient member 316. In the exemplified embodiment, the resilient member 316 is a coil spring, and more specifically a compression-type spring. However, the invention is not to be so limited and the resilient member 316 may be other types of springs such as extension, torsion, conical, barrel, wire, or the like. Furthermore, the resilient member 316 may not be a spring at all, but may be any device that can bias the valve apparatus 310 into one of the suction supply and oxygen supply positions (preferably biasing it into the suction supply state) while permitting the valve apparatus 310 to be altered from the biased position to the opposite position.

In the exemplified embodiment, the first valve body 310 is biased into the suction supply state by the resilient member 316. Specifically, the resilient member 316 forces the pedal 341, into the suction supply state (i.e., first position) such that the second contact portion 315 occludes the second conduit section 220. In this embodiment, a user must actuate the actuator apparatus 340 via a force applied to the pedal 341 to pivot the pedal 341 about the pivot axis C-C to alter the valve apparatus 310 and the rocker 313 to the oxygen supply state (i.e., second position) by pressing the pedal 341 with a sufficient force to overcome the bias of the resilient member 316. Because suction is more commonly used during a bronchoscopy and oxygen is generally only needed to treat hypoxia which may occur during a bronchoscopy, this may be a more preferred embodiment to have the pedal 341 biased into the suction supply state.

Although in the exemplified embodiment the resilient member 316 biases the valve apparatus 310 into the suction supply state, the invention is not to be so limited. In other embodiments, the resilient member 316 may bias the pedal 341 and the valve apparatus 310 into the oxygen supply state (such as by connecting the resilient member 316 to the base 360 and the second arm 321 rather than to the base 360 and the first arm 320 as shown in the exemplified embodiment). In still other embodiments, there may be multiple resilient members (one or more connected to the base 360 and the first arm 320 and one or more connected to the base 360 and the second arm 321) and an operator must apply a force to the foot pedal 341 to place the valve apparatus 310 into either the suction supply or oxygen supply states. In such an embodiment, the valve apparatus 310 may not be biased into either of the oxygen supply or suction supply states but rather may be biased into a neutral state until it is activated into one of the oxygen supply or suction supply states.

In certain embodiments, the foot pedal 341 may be color-coded to provide an easy guide for an operator to determine which state the pedal 341/valve apparatus 310 is in. Specifically, the foot pedal 341 may comprise a first color on a first side thereof and a second color on a second side thereof. When an operator applies foot pressure on the first color, the valve apparatus 310 may transition into the oxygen supply state. When an operator applies foot pressure on the second color, the valve apparatus 310 may transition into the suction supply state. Thus, colors may be used to guide an operator in his/her use of the system switching apparatus 300.

Figure 7:
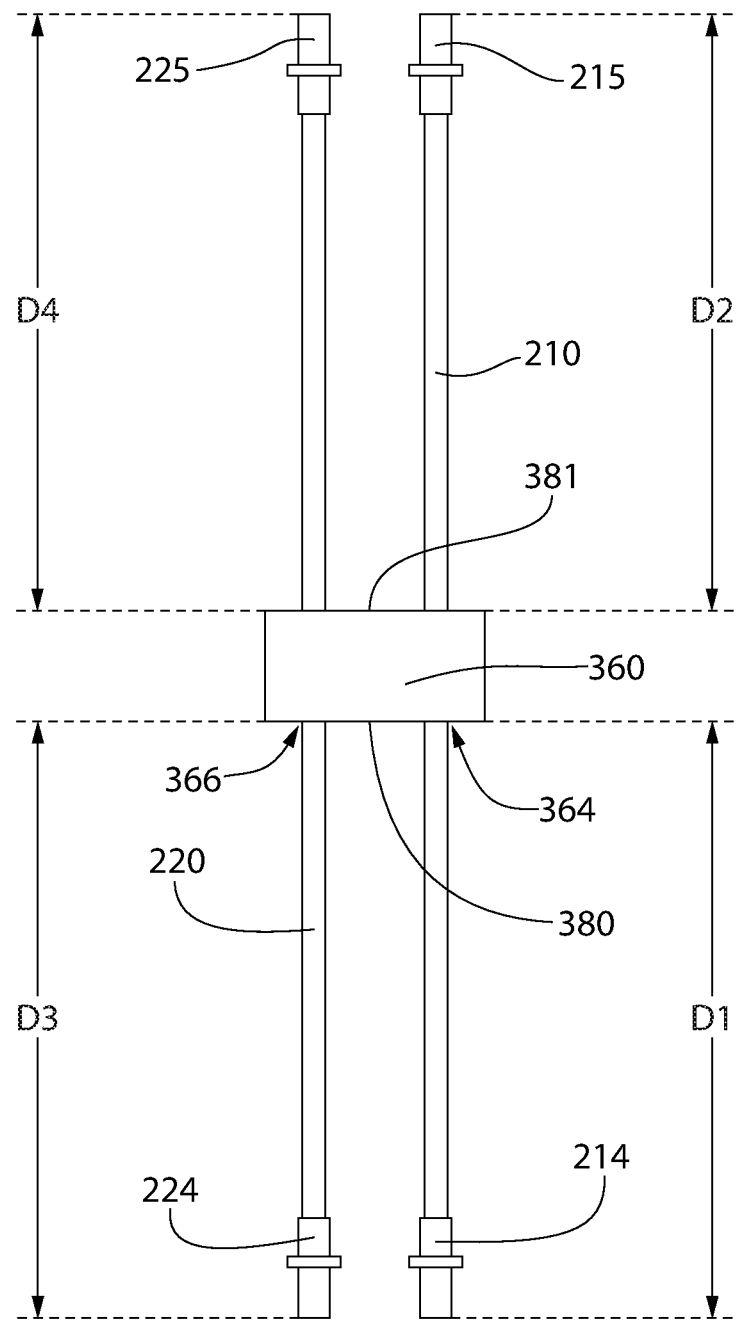
FIG. 7 is a top view of the switching apparatus of FIG. 6A.

Referring to FIG. 7, a top view of the base 360 with the first conduit section (i.e., first tube) 210 and the second conduit section (i.e., second tube 220) coupled thereto is provided. The base 360 has a first end 380 and a second end 381. The first and second channels 364, 366 extend through the base 360 from the first end 380 to the second end 381. In this embodiment, the first conduit section 210 is a first tube having a first coupler 214 on its first end and a second coupler 215 on its second end and the second conduit section 220 is a second tube having a first coupler 224 on its first end and a second coupler 225 on its second end, as described with reference to FIG. 4. Of course, as noted above the first conduit section 210 may be formed from more than one tube and the second conduit section 220 may be formed from more than one tube. For example, the first conduit section 210 may include a first tube coupled to the first end 380 of the base 360 and a second tube coupled to the second end 381 of the base 360 with the second conduit section 220 having a similar arrangement. In such an embodiment, the tubes would not extend through the base 360, although in an embodiment whereby the first and second conduit sections 210, 220 are formed from a single tube the single tube would extend through the base 360. The base 360 is illustrated generically in this view and the pedal is not illustrated at all in this view, but it should be appreciated that the specific structural details of those components may be as described above.

The first and second conduit sections or tubes 210, 220 may be fixedly coupled to the base 360 or they may be removably/detachably coupled to the base 360. In use, the first couplers 214, 224 could be coupled directly to a vacuum source and an oxygen source, respectively. Alternatively, the first and second conduit sections 210, 220 could be indirectly coupled to the vacuum and oxygen sources by having another tube extending from the vacuum and oxygen sources to the first couplers 214, 224. Furthermore, in use the second couplers 215, 225 may be coupled to a flow converger (such as the flow converger 250a of FIG. 5A) and a separate tube may extend from the flow converger to the bronchoscope as described herein.

In the exemplified embodiment, the first conduit section or first tube(s) 210 protrudes a first distance D1 from the first end 380 of the base 360 and protrudes a second distance D2 from the second end 381 of the base 360. Similarly, the second conduit section or second tube(s) 220 protrudes a third distance D3 from the first end 380 of the base 360 and a fourth distance D4 from the second end 381 of the base 360. In the exemplified embodiment, each of the first, second, third, and fourth distances D1-D4 are the same, although this is not required in all embodiments and some or all of the first, second, third, and fourth distances D1-D4 may be different from the others. In certain embodiments, each of the first, second, third, and fourth distances D1-D4 may be equal to or less than five feet, or equal to or less than four feet, or equal to or less than three feet, or equal to or less than two feet, or equal to or less than one foot.

Figure 8A:
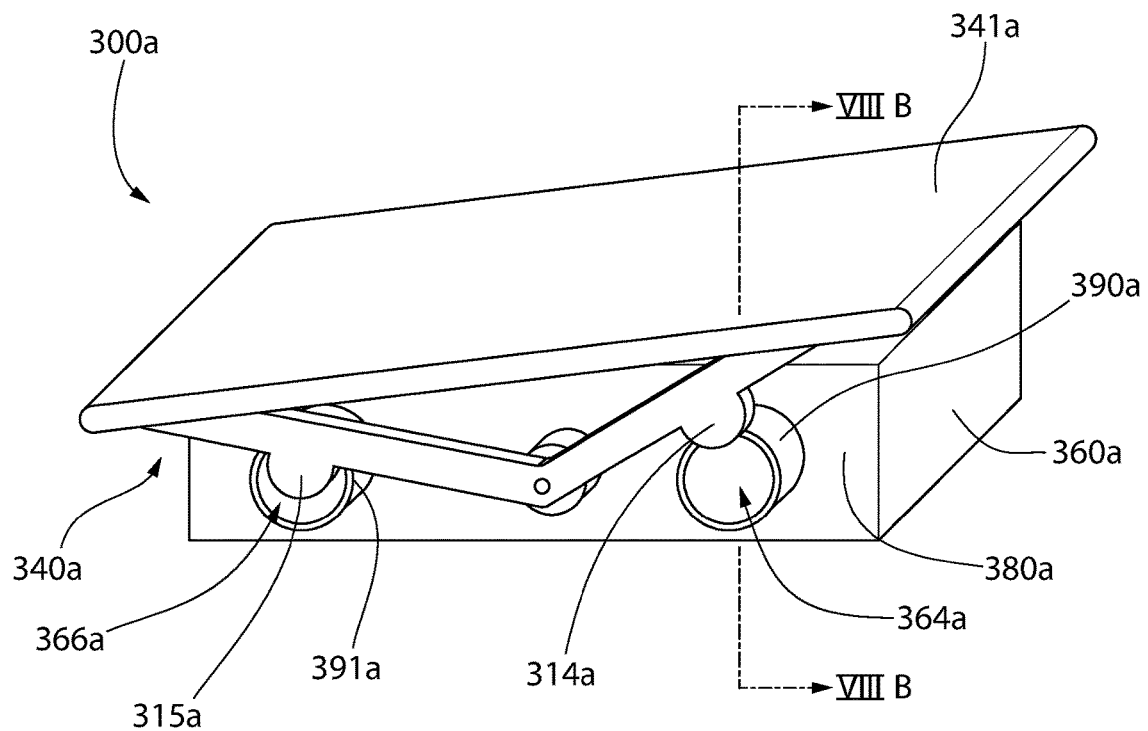
FIG. 8A is a perspective view of a switching apparatus in accordance with an alternative embodiment.
Figure 8B:
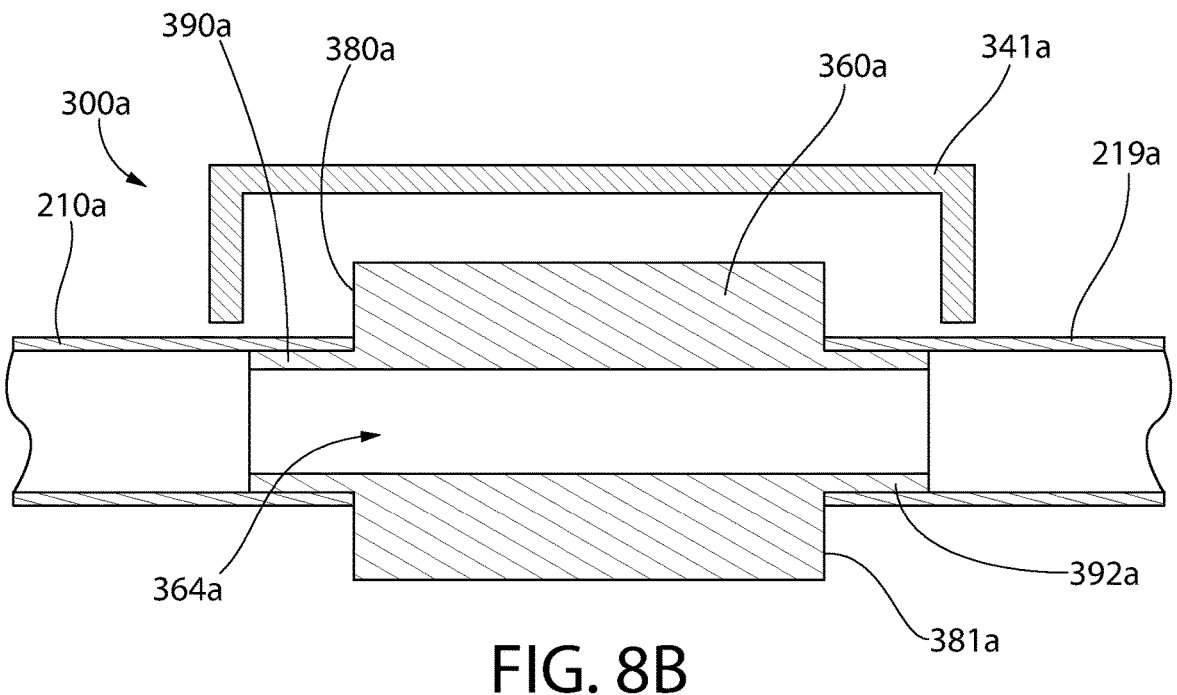
FIG. 8B is a cross-sectional view taken along line VIII-VIII of FIG. 8A.

Referring now to FIGS. 8A and 8B, a switching apparatus 300a is illustrated in accordance with a first alternative embodiment of the present invention. The structure and operation of the switching apparatus 300a is very similar to that which has been described above with regard to the switching apparatus 300. Thus, only the differences between the switching apparatus 300a and the switching apparatus 300 will be described herein, it being understood that the description above relating to the details of the switching apparatus 300 are otherwise applicable.

The switching apparatus 300a comprises a base 360a and a pedal 341a that is operably coupled to the base 360a. The interaction between the pedal 341a and the base 360a is similar to that which was described above. The base 360a has a first end 380a and a second end 381a opposite the first end 380a. The base 360a comprises a first channel 364a extending from a first opening on the first end 380a of the base 360a to a second opening on the second end 381a of the base 360a and a second channel 366a extending form a first opening on the first end 380a of the base 360a to a second opening on the second end 381a of the base 360a.

Furthermore, in this embodiment a first coupling member 390a extends from the first end 380a of the base 360a adjacent to the first channel 364a and a second coupling member 391a extends from the first end 380a of the base 360a adjacent to the second channel 366a. Similar coupling members may also extend from the second end 381 of the base 360a, such as the coupling member 392a shown in FIG. 8B. In this embodiment, the first and second coupling members 390a, 391a are tube-shaped protrusions that are formed integrally with the base 360a and are fluidly coupled to (and/or form a part of) the first and second channels 364a, 366a, respectively. Of course, the first and second coupling members 390a, 391a need not be integrally formed with the base 360a in all embodiments, but could be separate components that are either fixedly (i.e., non-detachably) coupled to the base 360a or separate components that are detachably coupled to the base 360a.

The first and second coupling members 390a, 391a make it easy for an end-user to readily couple a tube to the base 360a to start a bronchoscopy procedure. Specifically, as seen in FIG. 8B, a first tube 210a is coupled to the first coupling member 390a simply by sliding the first tube 210a over the first coupling member 390a. The first tube 210 can then be coupled, either directly or indirectly, to a vacuum or oxygen source. Similarly, the second tube 219a is coupled to the third coupling member 392a by simply sliding the second tube 219a over the third coupling member 392a. The second tube 219a can then be coupled, indirectly via a flow converger and another tube, to the bronchoscope as has been described herein. Tubes can similarly be coupled to the second coupling member 391a. Thus, this embodiment allows for a plug-and-play type arrangement whereby tubes can easily be coupled to the switching apparatus 300a.

In this embodiment, the tubes do not extend through the channels 364a, 366a of the base 360a, but rather the channels 364a, 366a of the base 360a form a part of the fluid flow path in addition to the tubes. Thus, when vacuum or oxygen is being supplied, the fluid will flow through the tubes and through the channels 364a, 366a in the base 360a. Because the channels 364a, 366a form a part of the fluid flow path, the channels 364a, 366a are fully enclosed other than the openings in the first and second ends 380a, 381a of the base 360a. Specifically, the first and second openings in the first and second ends 380a, 381a of the base 360a are the only passageways into the first and second channels 364a, 366a. This is necessary to ensure that the oxygen and suction are able to flow from the source to the bronchoscope and vice versa as the case may be. In this embodiment, because the fluid flows directly through the base 360a, the switching apparatus 300a should be disposed of after each use to prevent cross-contamination between patients.

Moreover, in this embodiment the coupling members 390a, 391a, 392a may be formed of a rigid material, such as a hard plastic, metal, or the like. It should be noted that the base 360a (as well as the base 360 described above and any other base described herein) may also be formed of a rigid material such as a hard plastic, metal, or the like. Thus, due to the coupling members 390a, 391a, 392a being formed of a rigid material, they are unable to be compressed by the first and second contact portions 314a, 315a of the actuator apparatus 340a. Rather, the first and second contact portions 314a, 315a should be positioned in such a way that they contact the tubes that are connected to the coupling members 390a, 391a, 392a because the tubes are compressible and can thereby be occluded using the actuator apparatus 340a in the manner described herein. Thus, the first and second contact portions 314a, 315a should be positioned beyond the coupling members 390a, 391a, 392a to facilitate the required compression and occlusion of the tubes. Of course, the coupling members 390a, 391a, 392a could be formed of a flexible material such as being formed of the same material as the tubes, in other embodiments.

Operation of the actuator apparatus 340a is similar to that which was described above with regard to the actuator apparatus 340. In this embodiment, when the pedal 341a is in the first state, the second contact portion 315a is located adjacent to the first opening of the second channel 366a and when the pedal 341a in the second state, the first contact portion 314a is located adjacent to the first opening of the first channel 364a. Furthermore, in the first state the second contact portion 315a is spaced a distance from the first opening of the second channel 366a, the distance being greater than the length of the first coupling member 390a. Similarly, in the second state the first contact portion 314a is spaced a distance from the first opening of the first channel 364a, the distance being greater than the length of the second coupling member 391a.

Figure 9A:
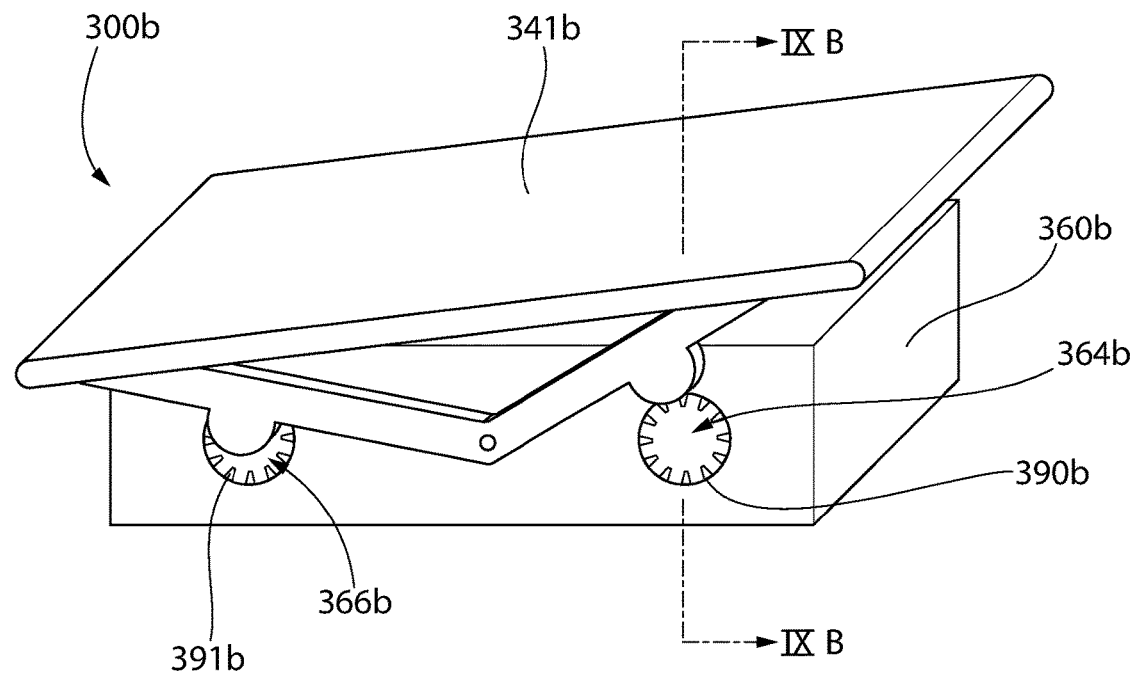
FIG. 9A is a perspective view of a switching apparatus in accordance with another alternative embodiment.
Figure 9B:
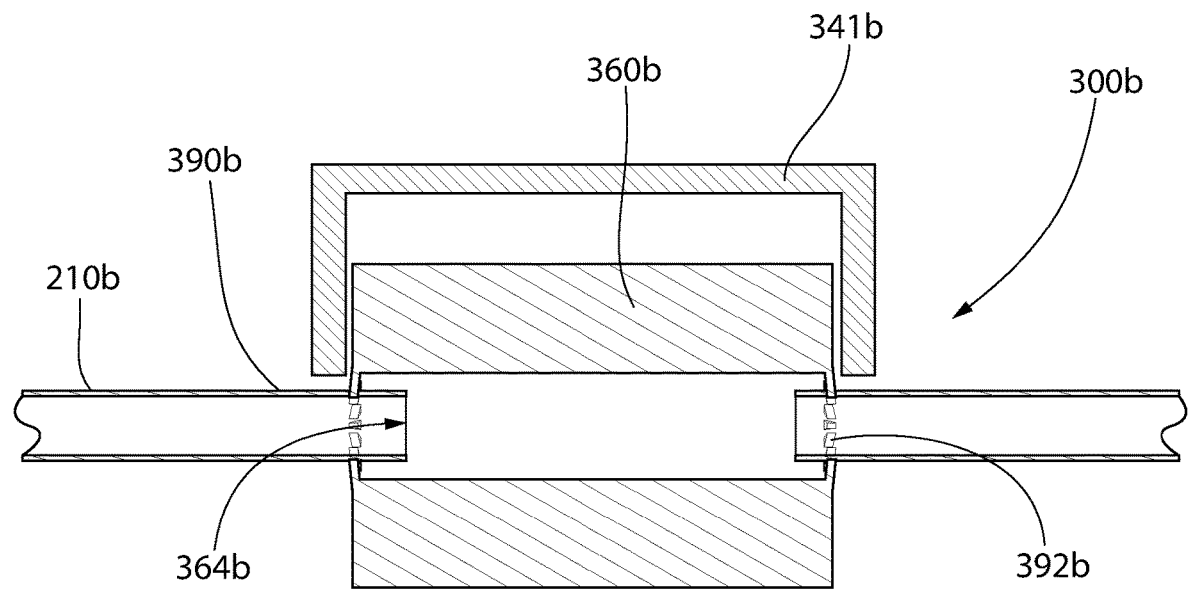
FIG. 9B is a cross-sectional view taken along line IX-IX of FIG. 9A.

Referring now to FIGS. 9A and 9B, a switching apparatus 300b is illustrated in accordance with a second alternative embodiment of the present invention. The structure and operation of the switching apparatus 300b is very similar to that which has been described above with regard to the switching apparatus 300 and the switching apparatus 300a. Thus, only the differences between the switching apparatus 300b and the switching apparatuses 300, 300a will be described herein, it being understood that the description above relating to the details of the switching apparatuses 300, 300a are otherwise applicable.

The main difference in this embodiment relative to the switching apparatus 300a previously described is with regards to the structure of the coupling members 390b, 391b, 392b. Specifically, in this embodiment the coupling members 390b, 391b, 392b comprises teeth or fingers that extend inwardly towards the respective channels 364b, 366b. Thus, when a tube 210b is inserted into the channel 364b, the teeth or fingers grip the tube 210b to thereby couple the tube 210b to the base 360b. Although the tube 210b can be retracted from the channel 364b with a pulling force, it will be retained in its coupled to the base 360b state during normal operation. This allows for another simple plug-and-play type embodiment whereby a user/operator simply needs to couple the tubes to the switching apparatus 300b and to the sources of oxygen and vacuum and to the bronchoscope and to then start the bronchoscopy procedure.

Figure 10:
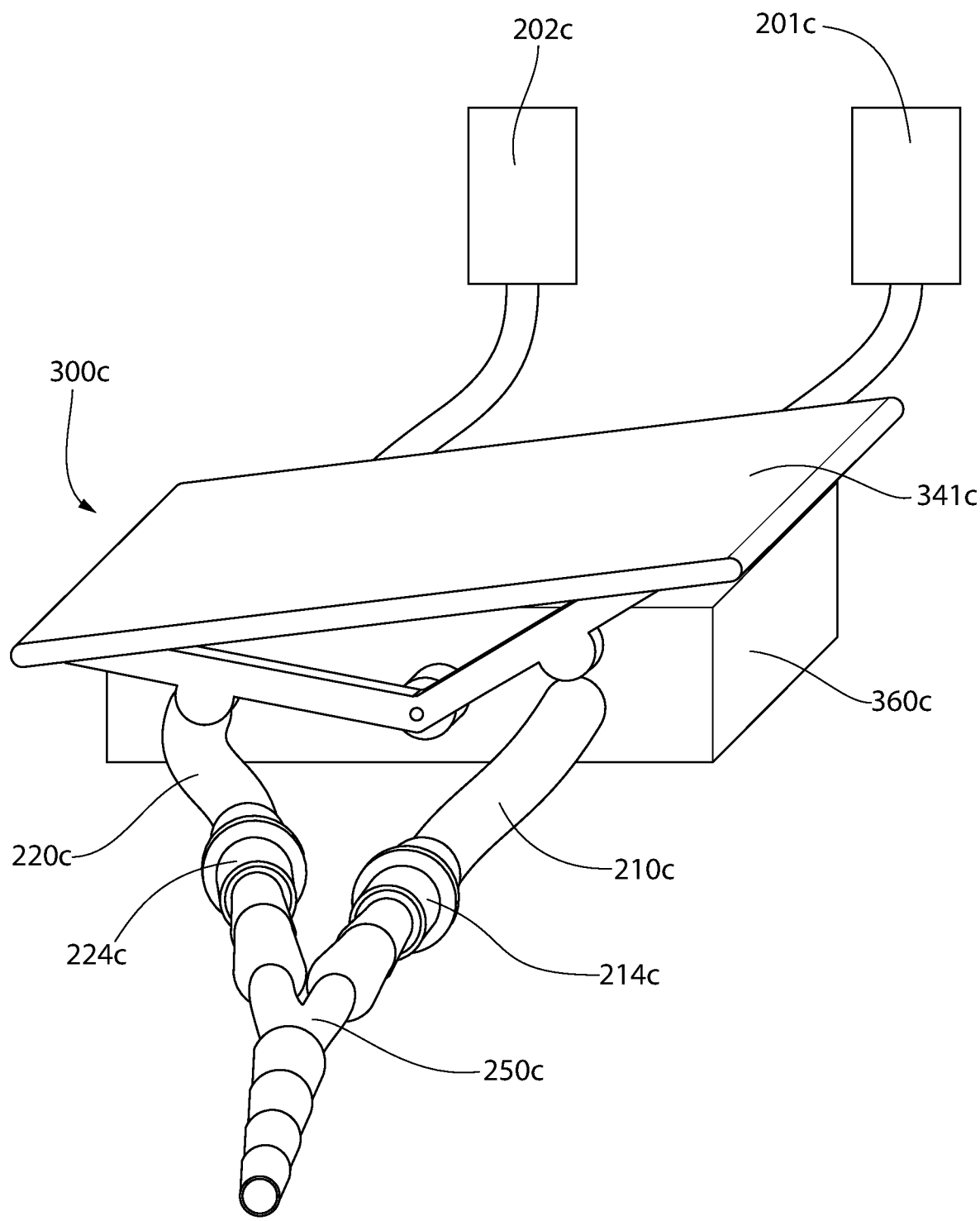
FIG. 10 is a perspective view of a switching apparatus in accordance with still another embodiment.

Referring now to FIG. 10, a switching apparatus 300c is illustrated in accordance with a third alternative embodiment of the present invention. The structure and operation of the switching apparatus 300c is very similar to that which has been described above with regard to the switching apparatuses 300, 300a, 300b. Thus, only the differences between the switching apparatus 300c and the switching apparatuses 300, 300a, 300b will be described herein, it being understood that the description above relating to the details of the switching apparatuses 300, 300a, 300b are otherwise applicable.

In this embodiment, a first tube 210c and a second tube 220c are coupled to the base 360c of the switching apparatus 300c. The first tube 210c terminates in a first coupler 214c and the second tube 220c terminates in a second coupler 224c. The first and second tubes 210c, 220c may be integrally formed with the base 360c in some embodiments. In other embodiments, the first and second tubes 210c, 220c may be non-detachably fixed to the base 360c. For example, the first and second tubes 210c, 220c may be non-detachably fixed to the base 360c by using adhesive to couple the first and second tubes 210c, 220c to the base 360c. Alternatively, the first and second tubes 210c, 220c may be ultrasonically welded or otherwise affixed to the base 360c in a manner that prevents a user from separating the first and second tubes 210c, 220c from the base 360c without breaking the tubes 210c, 220c and/or the base 360c. The base 360c may be sold with the first and second tubes 210c, 220c already coupled thereto.

In this embodiment, the flow converger 250a depicted in FIG. 5A and described above is coupled to the first and second tubes 210c, 220c, respectively. Specifically, one of the legs of the flow converger 250a is coupled to the first tube 210c, another one of the legs of the flow converger 250a is coupled to the second tube 220c, and the third leg of the flow converger 250a is available for coupling to another tube (not illustrated, but similar to the third conduit section 230 described above) that will extend from the third leg of the flow converger 250a to the bronchoscope. Furthermore, as illustrated in FIG. 10, the opposite sides of the first and second tubes 210c, 220c are coupled to a vacuum source 201c and an oxygen source 202c, respectively. Thus, if the second tube 220c is compressed into occlusion, vacuum will be supplied from the vacuum source 201c through the tube 210c, through the flow converger 250a, and to another tube, not shown, that extends from the flow converger 250a to the bronchoscope. If the first tube 210c is compressed into occlusion, oxygen will be supplied from the oxygen source 202c through the tube 220c, through the flow converger 250a, and to another tube, not shown, that extends from the flow converger 250a to the bronchoscope.

Figure 11:
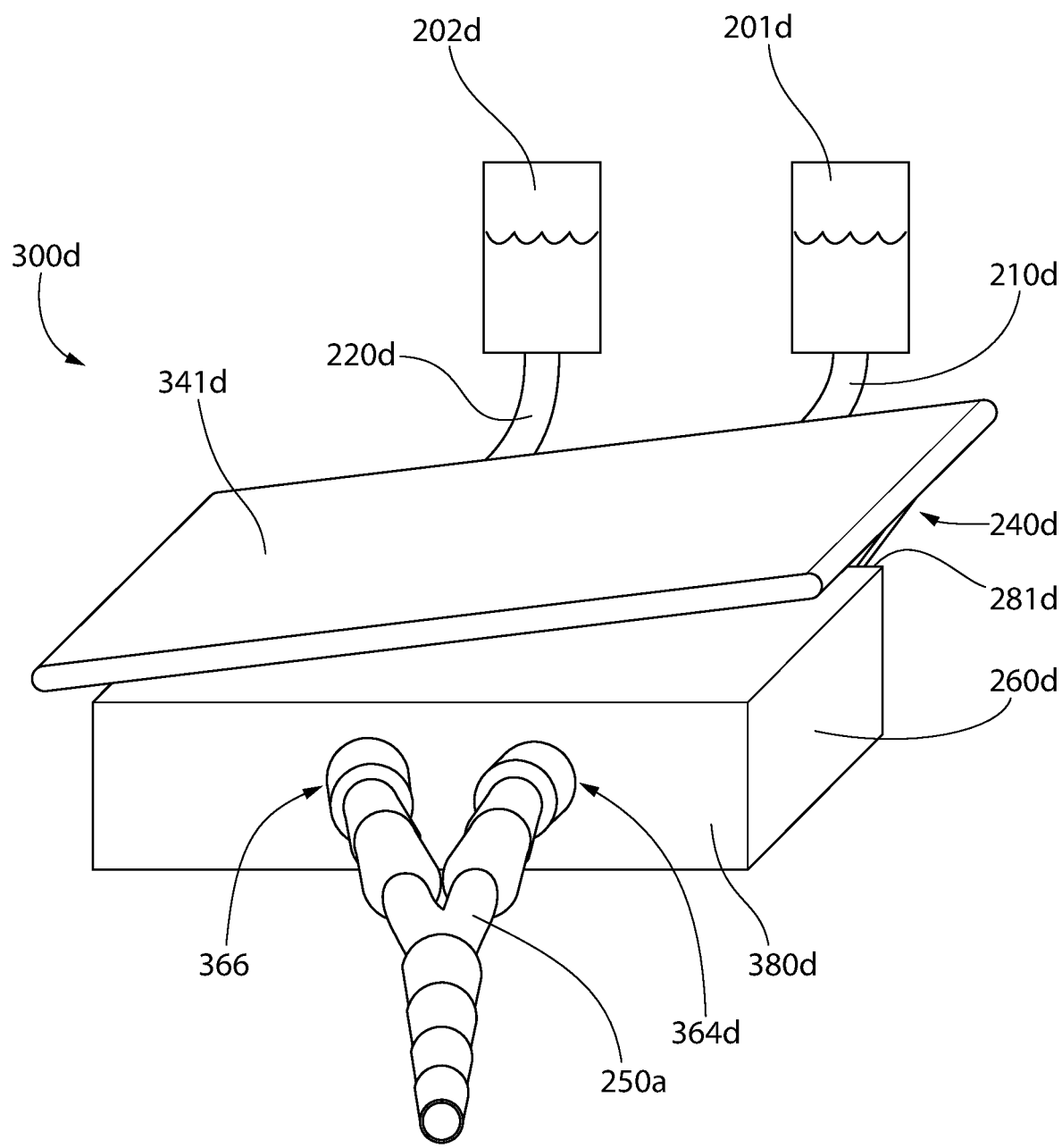
FIG. 11 is a perspective view of a switching apparatus in accordance with a further embodiment.

Referring now to FIG. 11, a switching apparatus 300d is illustrated in accordance with a third alternative embodiment of the present invention. The structure and operation of the switching apparatus 300d is very similar to that which has been described above with regard to the switching apparatuses 300, 300a, 300b, 300c. Thus, only the differences between the switching apparatus 300d and the switching apparatuses 300, 300a, 300b, 300c will be described herein, it being understood that the description above relating to the details of the switching apparatuses 300, 300a, 300b, 300c are otherwise applicable.

This embodiment is identical to the one previously described with reference to FIG. 10 except that there are no tubes extending from the first end 380d of the base 360d. Rather, in this embodiment the flow converger 250a is coupled directly to the base 360d, and more specifically to the openings of the first and second channels 364d, 366d of the base 360d. The flow converger 250a may be non-detachably fixed to the base 360d, such as by using adhesives, ultrasonic welds, clamps, bolts, fasteners, or the like. Alternatively, the flow converger 250a may be detachably coupled to the base 360d. In some embodiments, the switching apparatus 300d may be sold with the flow converger 250a already coupled thereto so that all that an end user needs to do is connect a tube from the bronchoscope to the free port of the flow converger 250a.

As shown, there are first and second tubes 210d, 220d coupled to and extending from the second end 381d of the base 360d. The first tube 210d extends from the base 360d to the vacuum source 201d. The second tube 220d extends from the base 360d to the oxygen source 202d, respectively. In this particular embodiment, the pedal 341d is positioned in such a manner that the contact portions (not illustrated, but similar to that which was described above) of the actuator apparatus 340d are located between the second end 381d of the base 360d and the vacuum and oxygen sources 201d, 202d. As a result, the contact portions of the actuator apparatus 340d are able to selectively compress one of the first and second tubes 210d, 220d into occlusion similar to that which has been described above. It should be appreciated that the first and second contact portions of the actuator apparatus for any of the embodiments described herein may be positioned to compress the tubes into occlusion at a location that is either: (1) between the vacuum and oxygen sources and the base; or (2) between the base and the bronchoscope.

Figure 12:
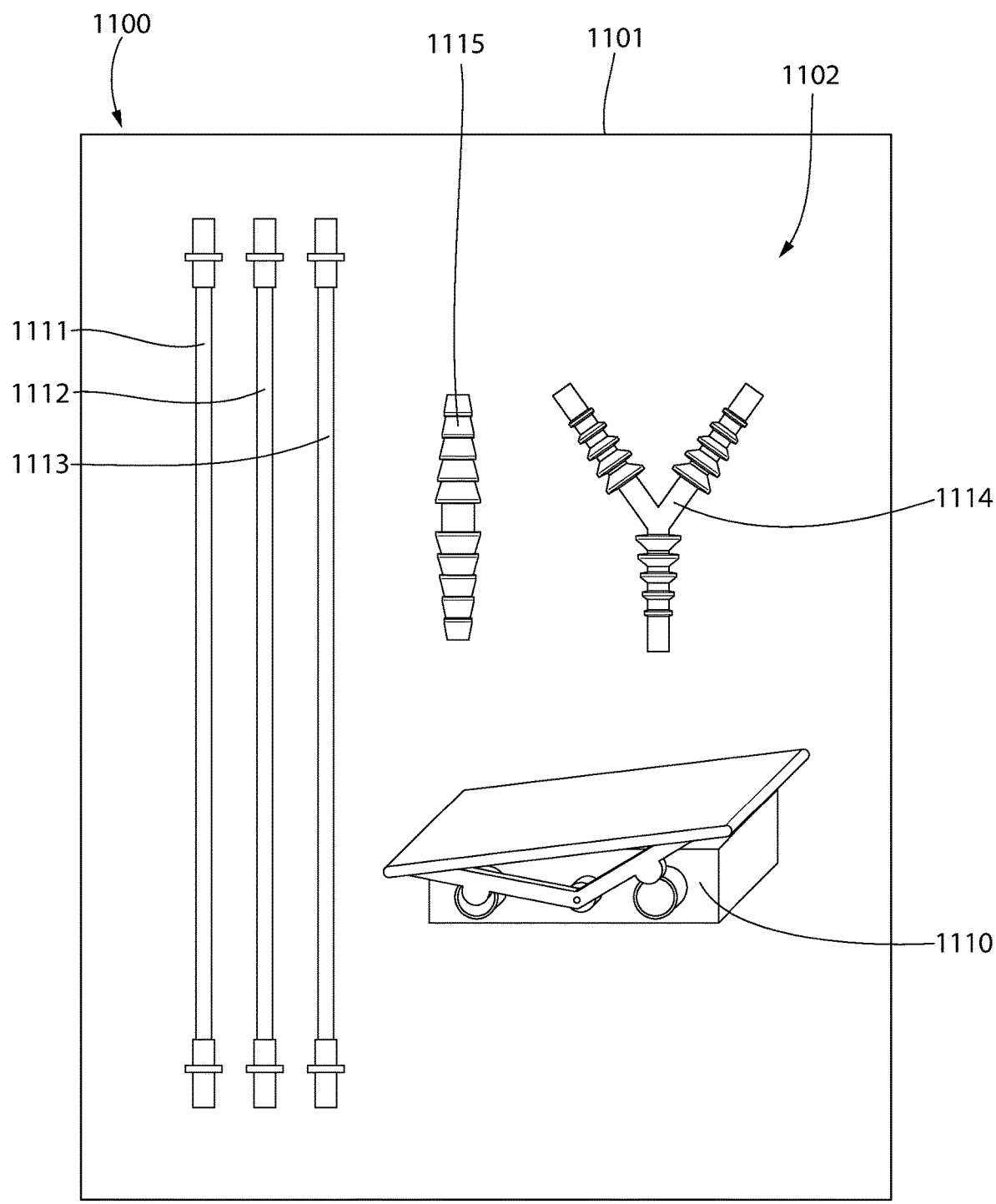
FIG. 12 is a schematic view of a kit that includes the switching apparatus, several lengths of tube, and couplers.

FIG. 12 illustrates a kit of parts 1100 for performing a bronchoscopy. The kit of parts 1100 includes all of the components required for an operator or user to perform a bronchoscopy, other than the bronchoscope itself. However, in other embodiments the kit of parts 1100 may also include a bronchoscope. By having all of the components placed together in a single kit, an assistant in an operating room can simply grab the necessary kit of parts 1100, attach the tubes as needed, and hand the bronchoscope to the doctor/operator to begin the bronchoscopy procedure.

In the exemplified embodiment, the kit of parts 1100 comprises a package 1101 having an interior cavity 1102. The package 1102 may be a plastic bag or the like or a similar type holding device configured to hold the items required to perform a procedure such as a bronchoscopy. The package 1101 is preferably sealed with the interior cavity 1102 being sterile so that when the components are removed from the interior cavity 1102 they are also sterile and ready for immediate use. The kit of parts 1100 comprises a plurality of components located within the interior cavity 1102 of the package 1101.

Specifically, in the exemplified embodiment, within the interior cavity 1102 of the package 1101, there is a switching apparatus 1110 (which may be any of the switching apparatuses described herein), a first tube 1111, a second tube 1112, a third tube 1113, a flow converger 1114, and a coupler 1115. The coupler 1115 may be omitted from the package 1101 in some embodiments. Moreover, as noted above, a bronchoscope may also be included in the package 1101 in some embodiments. Furthermore, in other embodiments there may be more than three tubes included in the package 1101. For example, in some embodiments it may be required to have four, five, six, seven, or the like separate lengths of tube to properly facilitate the coupling between the switching apparatus 1110 and the sources of vacuum/oxygen and the bronchoscope.

To start a bronchoscopy, an assistant or doctor or operator would open the package 1101 and remove the parts from its interior cavity 1102. The user would then couple tubes to the switching apparatus 1110 and the bronchoscope and separately couple tubes to the switching apparatus 1110 and the sources of oxygen and vacuum. In some embodiments, this may require five tubes so that one tube extends from the switching apparatus 1110 to the oxygen source, one tube extends from the switching apparatus 1110 to the vacuum source, two tubes extend from the switching apparatus 1110 to the flow converger 1114, and one more tube extends from the flower converger 1114 to the bronchoscope. However, three tubes may also be possible if, for example, the first tube 1111 extends from the vacuum source, through the switching apparatus 1110, and to the flow converger 1114, the second tube 1112 extends from the oxygen source, through the switching apparatus 1110, and to the flow converger 1114, and the third tube 1113 extends from the flow converger 1114 to the bronchoscope. The manner in which the various components are to be coupled together should be readily appreciated and understood from the description set forth throughout this document. Some or all of the tubes may be pre-coupled to the switching apparatus 1110 within the package 1101 or they may be retained separately within the package 1101 so that they can be assembled by an end user.

Figure 13A:
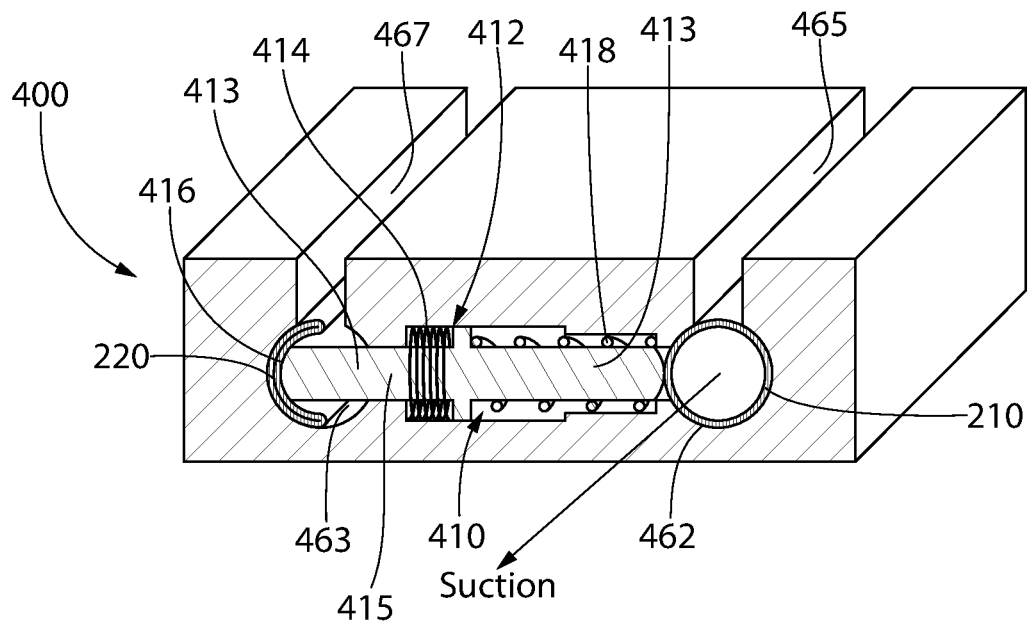
FIG. 13A is a schematic cross-sectional view of the switching apparatus of the system of FIG. 1 in accordance with another embodiment of the present invention, with the valve apparatus in a suction supply state.
Figure 13B:
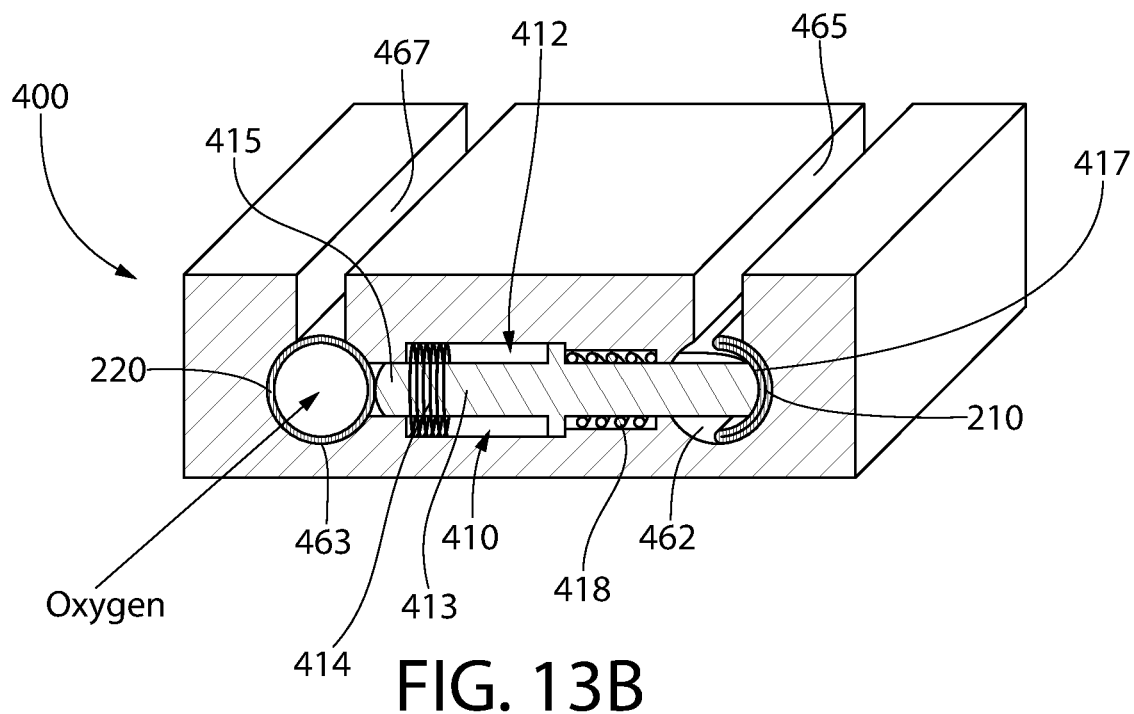
FIG. 13B is a schematic cross-sectional view of the switching apparatus of FIG. 13A with the valve apparatus in an oxygen supply state.

Referring to FIGS. 1, 13A, and 13B, an alternate embodiment of a switching apparatus 400 that may be used in accordance with the disclosure set forth herein will be described. Many features of the switching apparatus 400 are identical or similar to features of the switching apparatus 300 that has been described above. Thus, it should be appreciated that much of the description of the switching apparatus 300 is also applicable to the switching apparatus 400. Features of the switching apparatus 400 that are the same as features of the switching apparatus 300 will not be described in detail herein, it being understood that the description of the switching apparatus 300 provided above is applicable.

The switching apparatus 400 comprises a first conduit receiving section 462 and a second conduit receiving section 463 much like these same features of the switching apparatus 400. A first entry slot 465 extends from the first conduit receiving section 462 and a second entry slot 467 extends from the second conduit receiving section 463. Thus, the first conduit section 210 of the multi-fluid conduit apparatus 200 nests within the first conduit receiving section 462 and the second conduit section 220 of the multi-fluid conduit apparatus 200 nests within the second conduit receiving section 463.

In this embodiment, the switching apparatus 400 comprises a valve apparatus 410 and an actuator apparatus (not shown). The valve apparatus 410 comprises a first valve body 412 that comprises a solenoid 413. In the exemplified embodiment, the solenoid 413 is an electromechanical solenoid comprising an electrical coil 414 that surrounds a ferromagnetic core 415. The electrical coil 415 is operably coupled to a controller (not shown) that is operably coupled to the actuator apparatus (not shown). An embodiment showing a controller is provided in FIG. 16 and will be described in detail below.

In this embodiment, the solenoid 413 can be translated by the actuator apparatus between (1) a first position in which a first end 416 of the solenoid 413 compresses the second conduit section 220 into occlusion (FIG. 13A); and (2) a second position in which a second end 417 of the solenoid 413 compresses the first conduit section 210 into occlusion (FIG. 13B). Although this embodiment shows a single solenoid 413 being used to occlude each of the first and second conduit sections 210, 220, in an alternate embodiment separate solenoids may occlude the first and second conduit sections 210, 220. In such an alternate embodiment, the first and second solenoids may each be operably coupled to a controller such that each can separately be actuated to occlude or not occlude one of the first and second conduit sections 210, 220. Such an embodiment may enable both of the first and second conduit sections 210, 220 to be occluded simultaneously or neither of them to be occluded at a given point in time.

In this embodiment, the valve apparatus 410 also comprises a resilient member 418. The resilient member 418 biases the valve apparatus 410 into the first position in which the first conduit 210 is open and the second conduit 220 is closed so that suction can be applied to the bronchoscope 100 and to the patient's airways but oxygen cannot be applied to the bronchoscope 100 and to the patient's airways in the biased state. In the exemplified embodiment, the resilient member 418 is a compression spring, although it can take other forms such as that which has been described above with reference to the resilient member 316. During operation, upon activation of the actuator an electric current will be passed through the solenoid 413, which will overcome the bias of the resilient member 418 (i.e., by compressing the spring as shown in the exemplified embodiment) to alter the valve apparatus 410 from the first position shown in FIG. 13A (first conduit 210 open and second conduit 220 closed/occluded) to the second position shown in FIG. 13B (first conduit 210 closed/occluded and second conduit 220 open). The valve apparatus 410 may then remain in the second position for a predetermined period of time, or alternatively until a second activation of the actuator (or activating a different actuator) to alter the valve apparatus 410 back into the first position.

In some embodiments, each of the first and second conduit sections 210, 220 may include a pre-weakened section that is in operable cooperation with the valve apparatus 310, 410. Thus, the portion of the first and second conduit sections 210, 220 that may be compressed into occlusion by the valve apparatus 310, 410 may be pre-weakened to enable that portion of the first and second conduit sections 210, 220 to more easily transition and be compressed into the occluded state. In some embodiments, the pre-weakened portion of the first and second conduit sections 210, 220 may be formed by a thin section of the first and second conduit sections 210, 220. In other embodiments, the pre-weakened portions of the first and second conduit sections 210, 220 may be formed by a collapsible coupler, a slit, a notch, or any other feature that may pre-weaken the portion of the first and second conduit sections 210, 220 that are acted upon by the valve apparatus 310, 410.

Figure 14:
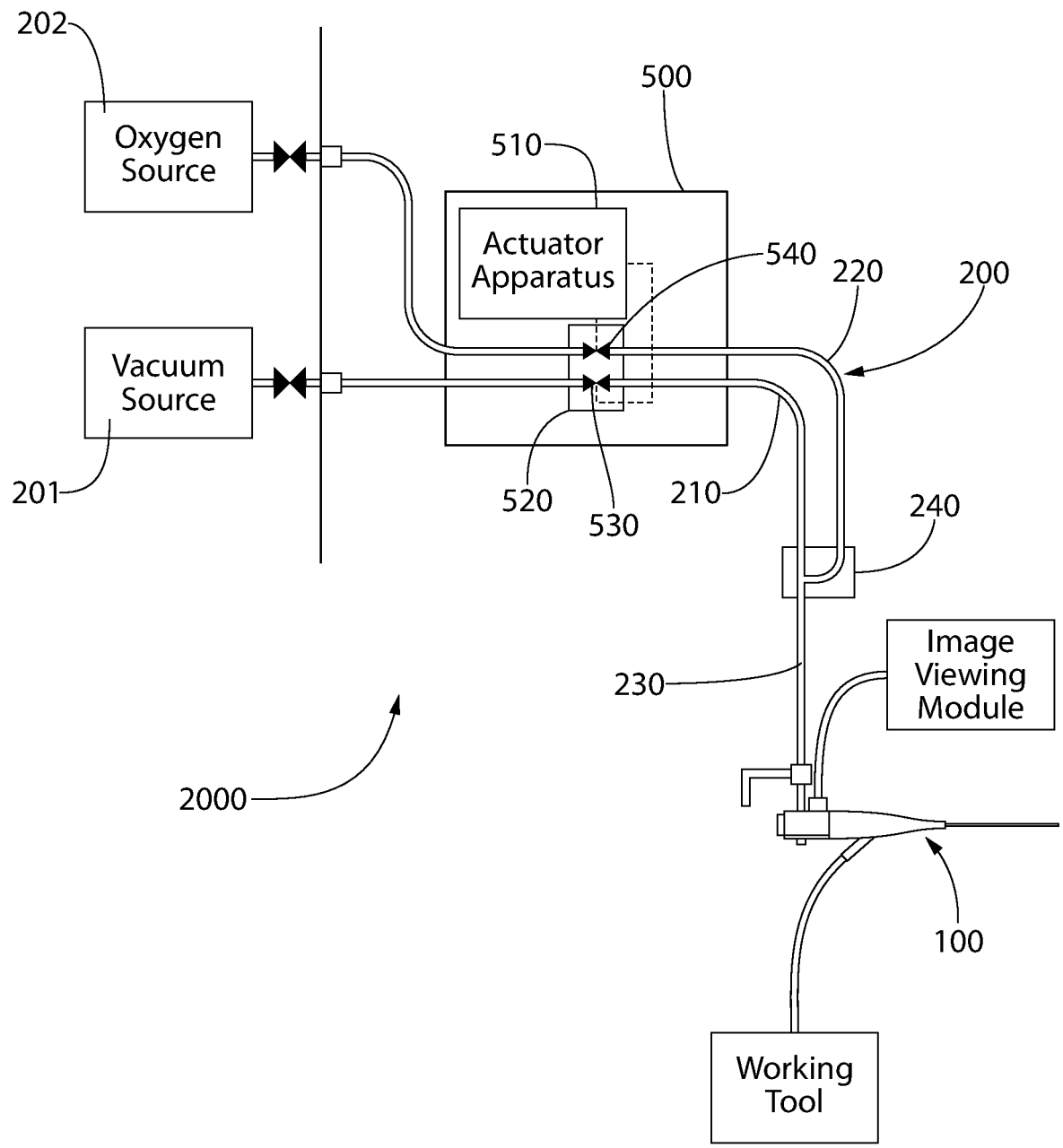
FIG. 14 is a schematic illustration of a system for performing a bronchoscope in accordance with a second embodiment of the present invention.

FIG. 14 illustrates a system for performing a bronchoscopy 2000 in accordance with an alternative embodiment of the present invention. Features of the system 2000 that are similar to features of the system 1000 will be similarly numbered, it being understood that the description of those similarly numbered features provided above with regard to the system 1000 is applicable to the system 2000. The main difference between the system 2000 of FIG. 14 and the system 1000 of FIG. 1 is that in the system 1000 of FIG. 1 there was a valve apparatus 310 having a singular valve body that could be altered between the first position (occluding the first conduit section 210) and the second position (occluding the second conduit section 220) whereas in the system 2000 of FIG. 14 there are two separate and distinct valves, each of which is coupled to one of the first and second conduit sections 210, 220.

In this embodiment, there is a switching mechanism 500 that comprises an actuator apparatus 510 and a valve apparatus 520, and in some embodiments the actuator apparatus 510 may comprise the valve apparatus 520. In this embodiment, the valve apparatus 520 comprises a first valve 530 operably coupled to the first conduit section 210 and a second valve 540 operably coupled to the second conduit section 220. The first and second valves 530, 540 may be any type of valve as has been described herein, including solenoid valves and any of various different types of mechanical valves. Each of the first and second valves 530, 540 is operably coupled to the actuator apparatus 510 so that actuation of the actuator apparatus 510 may alter the first and second valves 530, 540 between open and closed/occluded states.

These first and second valves 530, 540 may be alternatingly opened and closed to alternatingly supply vacuum and oxygen to a patient's airways during a bronchoscopy. In some embodiments, the first valve 530, which is operably coupled to the first conduit section 210, may be normally open and the second valve 540, which is operably coupled to the second conduit section 220, may be normally closed until the actuator apparatus 510 is actuated to close the first valve 530 and open the second valve 540. As mentioned above, this may be the preferred embodiment such that suction is being applied under normal circumstances until the actuator apparatus 510 is activated to apply oxygen. In other embodiments the opposite may be true and the first valve 530 may be normally closed while the second valve 540 is normally open. In still other embodiments, both of the first and second valves 520, 530 may be either normally open or normally closed. Thus, various permutations are possible and fall within the scope of the invention described herein.

In some embodiments, the first valve 530 may be a first pinch valve alterable between a closed state in which the first conduit section 210 is compressed into occlusion and an open state in which the first conduit section 210 is open. Similarly, the second valve 540 may be a second pinch valve alterable between a closed state in which the second conduit section 220 is compressed into occlusion and an open state in which the second conduit section 220 is open. When the first valve 530 is open and the first conduit section 210 is not occluded, vacuum or suction may be supplied into a patient's airways. When the second valve 540 is open and the second conduit section 220 is not occluded, oxygen may be supplied into a patient's airways. Of course, as mentioned above pinch and occlusion type valves are only one exemplary embodiment and other valves may be used including ball valves, butterfly valves, and the like.

Figure 15:
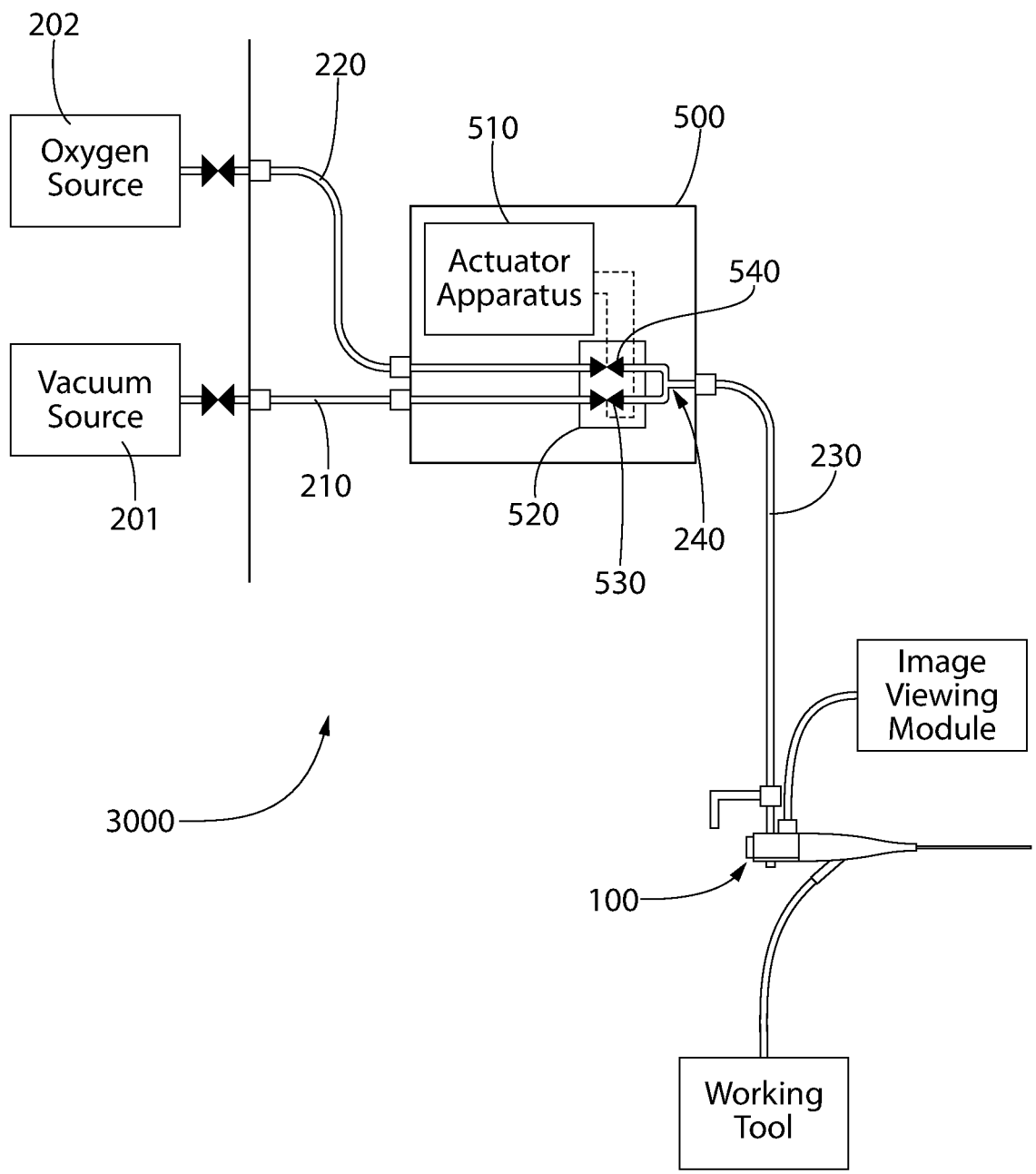
FIG. 15 is a schematic illustration of a system for performing a bronchoscope in accordance with a third embodiment of the present invention.

Referring to FIG. 15, a system for performing a bronchoscopy 3000 will be described in accordance with yet another embodiment of the present invention. Similar numbers are used to number features of the system 3000 as have been used in numbering the systems 1000, 2000. It should be understood that the description above is applicable for those features of the system 3000 that are not described in detail herein. The system 3000 is identical to the system 2000 except with regard to the location at which the first and second conduit sections 210, 220 connect to the third conduit section 230.

Specifically, in the system 2000 of FIG. 14, the flow converger 240 is located downstream of the switching apparatus 500. Similarly, in the system 1000 of FIG. 1, the flow converger 240 is located downstream of the switching apparatus 300. This means that two tubes are extending from both ends of the switching apparatus 300, as clearly shown in FIG. 1. Differently, in the system 3000 of FIG. 15, the flow converger 240 is located within the switching apparatus 500. Thus, although two tubes extend from one end of the switching apparatus 500 (so that one tube can be separately coupled to each of the vacuum and oxygen sources 201, 202), only a single tube extends from the other end of the switching apparatus 300. This is possible because the two tubes converge within the switching apparatus 500. As a result, a single tube need only be plugged into the outlet of the switching apparatus 500 and extend from the switching apparatus to the bronchoscope 100.

Figure 16:
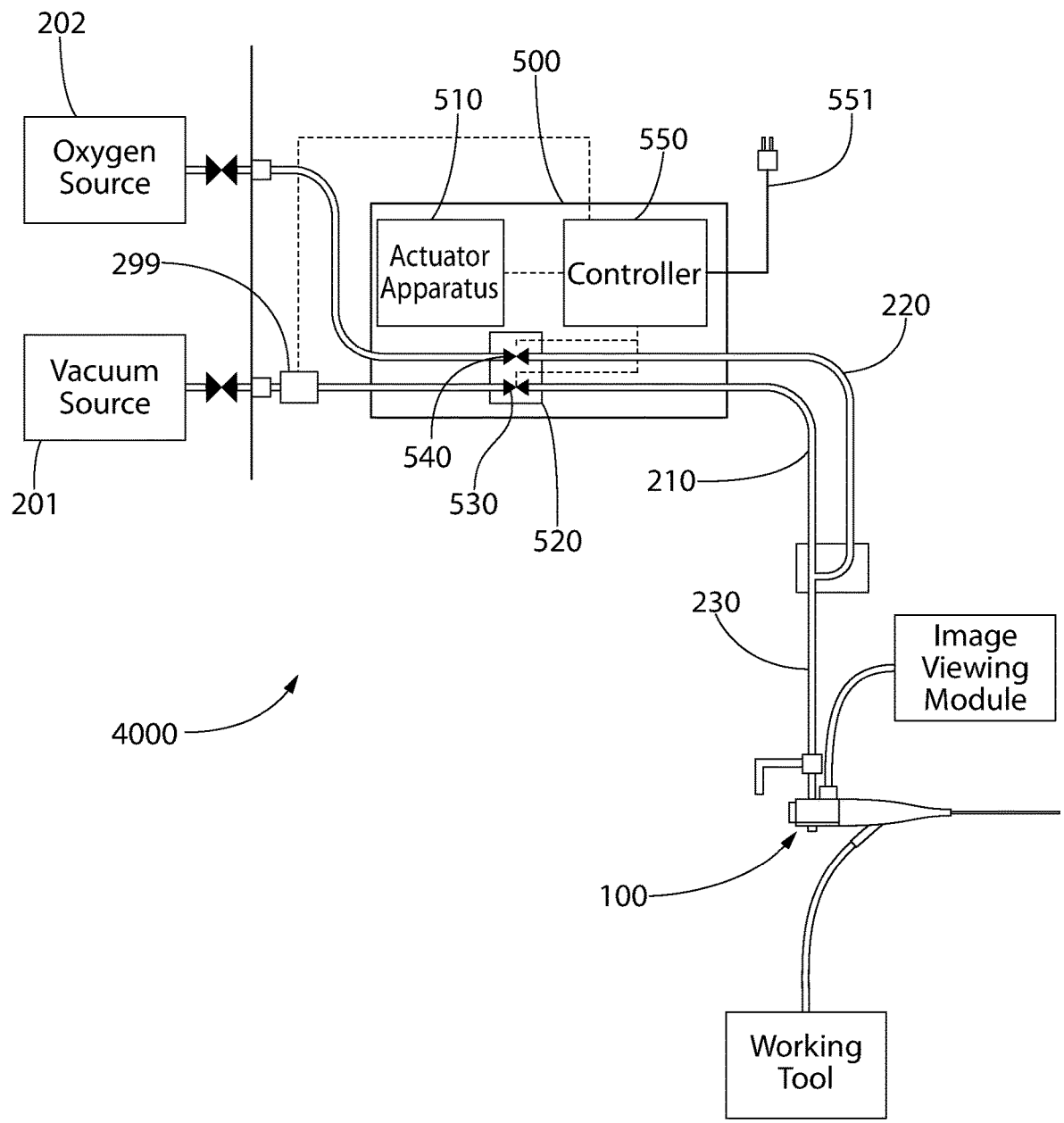
FIG. 16 is a schematic illustration of a system for performing a bronchoscope in accordance with a fourth embodiment of the present invention.

Referring to FIG. 16, a system for performing a bronchoscopy 4000 will be described in accordance with still another embodiment of the present invention. The system 4000 is similar to the systems 1000, 2000, 3000 previously described and thus only the differences will be described in great detail herein, it being understood that the descriptions of the systems 1000, 2000, 3000 are applicable for the similar components and features. Furthermore, features of the system 4000 that are similar to features of the system 1000, 2000, 3000 will be similarly numbered for ease of understanding. The system 4000 of FIG. 16 is similar to the system 2000 of FIG. 14 except for the addition of a controller 550 as a part of the switching apparatus 500. Thus, rather than having the actuator apparatus 510 coupled directly to the first and second valves 530, 540, in this embodiment the actuator apparatus 510 is coupled to the controller 550, which is in turn coupled to each of the first and second valves 530, 540. In the exemplified embodiment, the controller 550 is operably coupled to a power supply (not illustrated) via a power cord 551. However, in other embodiments the controller 550 may include a battery or may otherwise be coupled to a battery located within the switching apparatus 500 to power the controller 550.

In this embodiment, the actuator apparatus 510 and the valve apparatus 520 are both operably coupled to the controller 550. Thus, the controller 550 will receive instructions from the actuator apparatus 510 and will open and/or close the first and second valves 530, 540 of the valve apparatus 520 in response (or otherwise transition the valve apparatus 520 between suction supply and oxygen supply states as described herein, even where a single valve is used instead of two valves as shown in this embodiment). Thus, in this embodiment the actuator apparatus 510 may include a control panel having a user interface. An operator may select "oxygen supply" on the user interface, and in response the controller 550 will close the first valve 530 and open the second valve 540. An operator may select "vacuum supply" on the user interface, and in response the controller 550 will open the first valve 530 and close the second valve 540. Selection of "oxygen supply" and "vacuum supply" may be achieved via a touch screen, pressing a button associated with those functions, using voice commands, or the like. Of course, a user interface need not be included in all embodiments and other actuation techniques are possible such as a user pressing different buttons, toggling or sliding a switch, or the like depending on whether vacuum supply or oxygen supply is desired at any given time.

The controller 550 may in some embodiments comprise a processor and a memory device. The processor and memory device may be separate components, or the memory device may be integrated with the processor within the controller 550 as is the case in the exemplified embodiment. Furthermore, the controller 550 may include only one processor and one memory device, or it may include multiple processors and multiple memory devices.

The processor of the controller 550 may be any computer or central processing unit (CPU), microprocessor, microcontroller, computational device, or circuit configured for executing some or all of the processes described herein, including without limitation, opening and closing of all of the valves illustrated and described herein.

The memory device of the controller 550 may include, without limitation, any suitable volatile or non-volatile memory including random access memory (RAM) and various types thereof, read-only memory (ROM) and various types thereof, USB flash memory, and magnetic or optical data storage devices (e.g. internal/external hard disks, floppy discs, magnetic tape CD-ROM, DVD-ROM, optical disk, ZIP™ drive, Blu-ray disk, and others), which may be written to and/or read by the processor which is operably connected thereto. The memory device may store algorithms and/or calculations that can be used (by the processor) to determine when to open/close and activate/deactivate the various electrical components of the system described herein.

In the exemplified embodiment, the valve apparatus 520 includes the first valve 530 operably coupled to the first conduit section 210 and the second valve 540 operably coupled to the second conduit section 220. In this embodiment, the first and second valves 530, 540 may be separately and independently operated by the controller 550. Of course, in other embodiments the valve apparatus 520 may include a single valve, such as that which has been illustrated in FIGS. 13A and 13B, and the controller 550 may operate the single valve by moving it between the first position whereby it occludes the first conduit section 210 and the second position whereby it occludes the second conduit section 220. The incorporation of the controller 550 and the various connections enables the system 4000 to operate autonomously in some embodiments. However, operator interaction with the actuator apparatus 510 to control opening and closing of the first and second valves 530, 540 may be desired to ensure operation occurs in a desired manner based on the current circumstances that the operator is facing during a bronchoscopy procedure.

Still referring to FIG. 16, in this embodiment the system 4000 further includes a sensor 299 operably coupled to the multi-fluid conduit apparatus 200. More specifically, in the exemplified embodiment the sensor 299 is positioned along the first conduit section 210, although it may be coupled to the multi-fluid conduit apparatus 200 at other locations in other embodiments. In some embodiments, the sensor 299 may be a carbon dioxide sensor configured to measure carbon dioxide content of the air being drawn by the working channel 140 of the bronchoscope 100 when the system 4000 is in the vacuum/supply state. The sensor 299 is operably coupled to the controller 550 as shown. Thus, the controller 550 may be configured to automatically switch the valve apparatus 520 into the oxygen supply state upon the carbon dioxide measured by the sensor 299 being detected to be at or above a predetermined threshold.

Specifically, when the level of carbon dioxide in the patient's airways is too high (i.e., at or above the predetermined threshold), the patient may be suffering from hypercapnia, which may be treated by giving the patient oxygen. Thus, the system 4000 may automatically adjust to deal with hypercapnia and ensure that the patient has sufficient oxygen in his/her lungs by occluding the first conduit section 210 so that no suction is being applied to the patient's airways while opening the first conduit section 220 so that oxygen can be supplied to the patient's airways.

Figure 17:
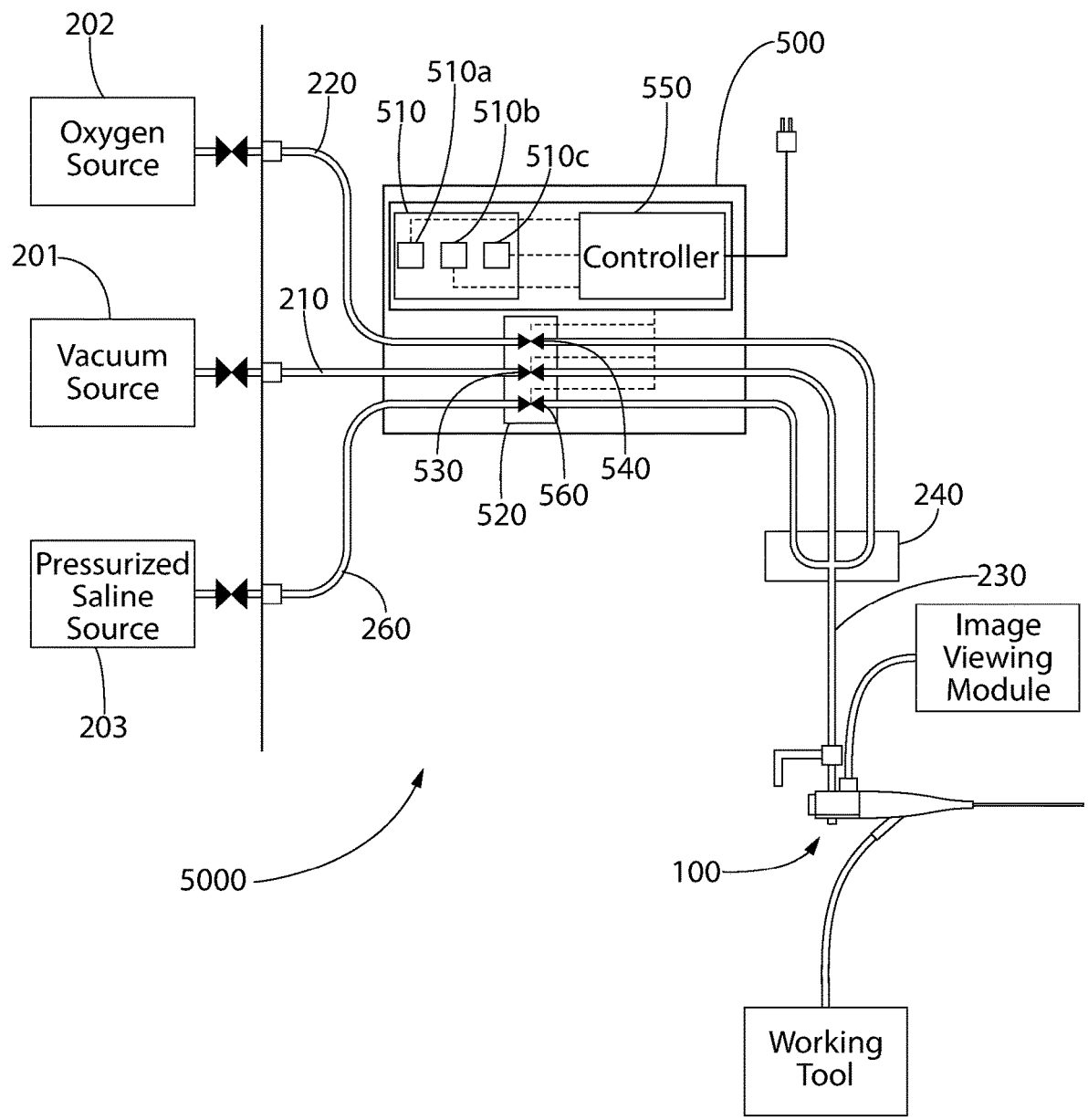
FIG. 17 is a schematic illustration of a system for performing a bronchoscope in accordance with a fifth embodiment of the present invention.

Referring now to FIG. 17, a system for performing a bronchoscopy 5000 is illustrated in accordance with yet another embodiment of the present invention. The system 5000 is similar to the system 4000 and thus for similar features a similar numbering scheme will be used. Some features of the system 5000 will not be described in detail herein, it being understood that the previous disclosure is applicable.

There are a couple of differences between the system 5000 and the system 4000. First, the multi-fluid conduit apparatus 200 of the system 50000 includes a fourth conduit section 260 that is operably and fluidly coupled to a saline source 203 (which may be pressurized to ensure saline flows to the working channel 140 of the bronchoscope 100 when all applicable valves are open without requiring any additional pumps or the like) and to the flow converger 240. Thus, each of the first, second, and fourth conduit sections 210, 220, 260 converge into the third conduit section 230. This flow convergence may take place within the switching apparatus 500 or external to it. Thus, in this embodiment not only can oxygen and suction be applied to the patient's airways during a bronchoscopy, but also saline. The valve apparatus 520 is therefore operably coupled to each of the first, second, and fourth conduit sections 210, 220, 260 of the multi-fluid conduit apparatus 200. In the exemplified embodiment, the valve apparatus 520 includes a first valve 530 operably coupled to the first conduit section 210, a second valve 540 operably coupled to the second conduit section 220, and a third valve 560 operably coupled to the fourth conduit section 260. However, a single valve that is operably coupled to each of the first, second, and third conduit sections 210, 220, 260 may be used in other embodiments.

Depending on which of the first, second, and third valves 530, 540, 560 is open will dictate which fluid (oxygen, suction, saline) is able to flow into the third conduit section 230 and hence also into the working channel 140 of the bronchoscope 100 and from there into the patient's airway. Specifically, if the first valve 530 is open and the second and third valves 540, 560 are closed, suction is applied to the patient's airway. If the second valve 540 is open and the first and third valves 530, 560 are closed, oxygen is applied to the patient's airway. If the third valve 560 is open and the first and second valves 530, 540 are closed, saline is applied to the patient's airway. Furthermore, more than one of the valves may be open at the same time. For example, the second and third valves 540, 560 may be opened at the same time, which will enable the simultaneous instillation of saline and oxygen that will spray and clean the distal end 131 of the insertion tube 130 of the bronchoscope 100, which may establish optimal vision and enhance an operator's ability to see inside the patient's airways. This may be desirable because at certain times during a bronchoscopy secretion or blood may obscure the operator's vision, and thus providing a simple technique for clearing the secretions and blood will shorten procedure time and increase effectiveness of the procedure.

Furthermore, the instillation of saline into the patient's airways may be beneficial when performing a Bronchoalveolar lavage (BAL). BAL is a medical procedure in which the bronchoscope 100 is passed through the mouth or nose and into the lungs and fluid (i.e., saline) is squirted into a small part of the lung and then collected for examination. This technique may be performed to diagnose lung disease and for other reasons. Thus, by connecting a saline source 203 to the working channel 140 of the bronchoscope 100 within the multi-fluid conduit apparatus 200, saline can readily and easily be applied into the lungs/airways for a BAL.

Furthermore, although a single actuator may be used as with the previously described embodiments, in this exemplified embodiment the actuator apparatus 510 includes a first actuator 510a, a second actuator 510b, and a third actuator 510c, each of which is operably coupled to the controller 550. In such embodiment, activating the first actuator 510a will cause the controller 550 to open or close the first valve 530, activating the second actuator 510b will cause the controller 550 to open or close the second valve 540, and activating the third actuator 510c will cause the controller 550 to open or close the third valve 560 (open it if it is closed and close it if it is open). In alternative embodiments, the first, second, and third actuators 510a-c may be coupled directly to the first, second, and third valves 530, 540, 560, respectively rather than to the controller 550. In such embodiment, manual activation of the first actuator 510a will open/close the first valve 530, manual activation of the second actuator 510b will open/close the second valve 540, and manual activation of the third actuator 510c will open/close the third valve 560.

In this embodiment, the actuator apparatus 510 is operably coupled to the valve apparatus 520 to alter the valve apparatus 520 between: (1) the suction supply state, wherein the oxygen source 202 and the saline source 203 are cut off from fluid communication with the third conduit section 230 while the vacuum source 201 is in fluid communication with the third conduit section 230; (2) the oxygen supply state, wherein the vacuum source 201 and the saline source 203 are cut off from fluid communication with the third conduit section 230 while the oxygen source 202 is in fluid communication with the third conduit section 230; and (3) a rinse state in which the vacuum source 201 is cut off from fluid communication with the third conduit section 230 and both the oxygen source 202 and the saline source 203 are in fluid communication with the third conduit section 210. Furthermore, there may also be a saline supply state, in which the vacuum source 201 and the oxygen source 202 are cut off from fluid communication with the third conduit section 230 while the saline source 203 is fluidly coupled to the third conduit section 230. The different states may be achieved by opening and closing the first, second, and third valves 530, 540, 560 using any of the techniques that have been discussed in detail herein above.

In certain embodiments, the controller 550 may be preprogrammed with certain algorithms to achieve various procedures during a bronchoscopy. In some embodiments, once the rinse state is activated, the controller 550 may be configured to automatically terminate the rinse state upon expiration of a predetermined period of time and return to one of the oxygen supply state or the suction supply state. This is because the rinse state is generally only used to clean the distal end 131 of the insertion tube 130 of the bronchoscope 100 and thus maintaining the rinse state for a long period of time is not needed and may be undesirable because it may be desired to minimize the amount of saline that is enabled to enter into the patient's airways. Thus, by automatically transitioning out of the rinse state after a predetermined period of time, the system 5000 may automatically ensure that excess saline is not being introduced into the patient's airways.

During operation, the insertion tube 130 of the bronchoscope 100 is inserted into a patient's airways. The working channel 140 of the bronchoscope 100 is operably coupled to the multi-fluid conduit 200, which in turn is operably coupled to the vacuum source 201 and the oxygen source 202 (and possibly also the saline source 203). During a bronchoscopy, the operator will activate one or more actuators to switch between: (1) having one of the vacuum source 201 or the oxygen source 202 in fluid communication with the working channel 140; and (2) having the other one of the vacuum source 201 and the oxygen source 202 in fluid communication with the working channel 140. Thus, activation of the actuators may occur while an instrument is located within the airways (i.e., in-situ) during a bronchoscopy procedure. Furthermore, when the system 5000 is used, the operator may also activate the actuators to have the saline source 203 in fluid communication with the working channel 140 either by itself for a BAL or in conjunction with the oxygen source 202 for a cleaning operation. As discussed herein, in some embodiments only one of the vacuum source 201 and the oxygen source 202 may be in fluid communication with the working channel 140 at a time.

In certain embodiments, during use when the second conduit section 220 is open, oxygen may flow into the working channel 140 of the bronchoscope 100 and into the patient's airway at a flow rate of 8 liters per minute. Of course, a flow rate less than 8 liters per minute is also possible and the flow rate may be modified as needed depending on the particular patient's needs. For example, in some embodiments the bronchoscopy may take place with a patient in ventilation with the patient unable to effectively remove air from his/her lungs. In such a situation, a flow rate of 8 liters per minute might be too much and thus a reduced flow rate would be desirable in such situations. The second conduit section 220 may include a pressure relief valve to automatically close the second conduit section 220 if the flow rate of the oxygen is too high for the particular patient or situation. Alternatively, the second conduit section 220 may include a manual shut-off valve to enable the operator to occlude or otherwise close the second conduit section 220 to avert this type of situation.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An apparatus for switching between fluid sources during a bronchoscopy, the apparatus comprising:
a base;
a first tube coupled to the base;
a second tube coupled to the base;
an actuator apparatus comprising:
a first contact portion;
a second contact portion;
a pedal pivotably coupled to the base; and
a resilient member;
wherein the actuator apparatus is alterable between: (1) a first state in which the second contact portion compresses the second tube into occlusion and the first tube is open; and (2) a second state in which the first contact portion compresses the first tube into occlusion and the second tube is open, wherein the pedal is configured to pivot between the first and second states, and wherein the resilient member is configured to bias the pedal into the first state.

2. The apparatus according to claim 1 wherein the first tube is configured to be fluidly coupled to a vacuum source and the second tube is configured to be fluidly coupled to an oxygen source.

3. The apparatus according to claim 1 wherein the first tube extends along a first axis and the second tube extends along a second axis, and wherein in the first state a portion of the second tube is compressed radially and in the second state a portion of the first tube is compressed radially.

4. The apparatus according to claim 1 further comprising a third tube fluidly coupled to each of the first and second tubes, the third tube configured to be fluidly coupled to a working channel of a bronchoscope.

5. The apparatus according to claim 1 wherein activation of the actuator apparatus transitions the pedal from the first state to the second state, and wherein upon cessation of the activation of the actuator apparatus, the pedal automatically transitions from the second state back to the first state.

6. The apparatus according to claim 1 further comprising a first channel formed through the base and a second channel formed through the base, at least a portion of the first tube positioned in the first channel and at least a portion of the second tube positioned in the second channel.

7. The apparatus according to claim 1 wherein the first and second tubes are non-detachably fixed to the base and wherein the apparatus is one-time use disposable.

8. The apparatus according to claim 1 wherein each of the first and second contact portions is integral with the pedal.

* * * * *